United States Patent
Hagen et al.

(10) Patent No.: US 8,639,372 B2
(45) Date of Patent: *Jan. 28, 2014

(54) AUTOMATED OPTICAL LENS PROCESSING SYSTEM, SUCH AS A SYSTEM FOR PROVIDING SUPPLEMENTAL INFORMATION TO LABORATORY TECHNICIANS

(71) Applicant: Digital Vision, Inc., Portland, OR (US)

(72) Inventors: Douglas S. Hagen, Portland, OR (US); Gordon Keane, Portland, OR (US)

(73) Assignee: Digital Vision, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/718,025

(22) Filed: Dec. 18, 2012

(65) Prior Publication Data

US 2013/0110273 A1    May 2, 2013

Related U.S. Application Data

(63) Continuation of application No. 12/644,454, filed on Dec. 22, 2009, now Pat. No. 8,340,799.

(51) Int. Cl.
  *G06F 19/00* (2011.01)
(52) U.S. Cl.
  USPC .......................................... 700/97; 715/771
(58) Field of Classification Search
  USPC ............... 700/97, 104, 110, 117; 705/26–27; 351/159
See application file for complete search history.

(56) References Cited

U.S. PATENT DOCUMENTS

| | | | |
|---|---|---|---|
| 4,185,897 | A | 1/1980 | Frieder |
| 4,573,121 | A | 2/1986 | Saigo et al. |
| 4,580,883 | A | 4/1986 | Shinohara |
| 4,710,193 | A | 12/1987 | Volk |
| 4,958,280 | A | 9/1990 | Pauly et al. |
| 5,368,790 | A | 11/1994 | Greshes |
| 5,485,399 | A | 1/1996 | Saigo et al. |
| 5,805,336 | A | 9/1998 | Dalzell et al. |
| 5,880,809 | A | 3/1999 | Lieberman et al. |
| 5,983,201 | A | 11/1999 | Fay |
| 6,019,470 | A | 2/2000 | Mukaiyama et al. |
| 6,051,091 | A | 4/2000 | Wood et al. |

(Continued)

FOREIGN PATENT DOCUMENTS

JP    2002133219    5/2002

OTHER PUBLICATIONS

"Announcing Sweep," Product brochure of Digital Vision, inc., www.thedvi.com (applicant herein), published before Aug. 10, 2010, 2 pgs.

(Continued)

*Primary Examiner* — Kidest Bahta
(74) *Attorney, Agent, or Firm* — Perkins Coie LLP

(57) ABSTRACT

An electronic lens processing system receives a lens prescription and performs lens calculations to create a work ticket for manufacturing the lens. Information that the system used to create the work ticket, such as data files for lens materials and machine settings for controlling lens manufacturing equipment, are stored. The work ticket includes a form that specifies work ticket calculations and/or a graphic of the lens or lenses to be manufactured. The system displays the work ticket on an electronic screen, and a laboratory technician can select elements from the work ticket to receive supplemental information on those elements to aid in processing the lens or determining why a lens prescription is not manufacturable.

20 Claims, 20 Drawing Sheets

(56) References Cited

U.S. PATENT DOCUMENTS

| | | |
|---|---|---|
| 6,058,373 A | 5/2000 | Blinn et al. |
| 6,082,856 A | 7/2000 | Dunn et al. |
| 6,089,713 A | 7/2000 | Hof et al. |
| 6,508,553 B2 | 1/2003 | Gao et al. |
| 6,637,880 B1 | 10/2003 | Yamakaji et al. |
| 6,736,506 B2 | 5/2004 | Izumitani et al. |
| 6,789,896 B2 | 9/2004 | Morris et al. |
| 6,792,401 B1 | 9/2004 | Nigro et al. |
| 6,871,955 B2 | 3/2005 | Yamakaji et al. |
| 6,902,271 B2 | 6/2005 | Perrott et al. |
| 7,029,116 B2 | 4/2006 | Roscini |
| 7,051,209 B1 | 5/2006 | Brickell |
| 7,054,836 B2 | 5/2006 | Christensen et al. |
| 7,111,938 B2 | 9/2006 | Andino et al. |
| 7,152,975 B2 | 12/2006 | Ho et al. |
| 7,188,082 B2 | 3/2007 | Keane et al. |
| 7,281,793 B2 | 10/2007 | D'Agostino |
| 7,353,738 B2 | 4/2008 | Chen |
| 7,419,261 B2 | 9/2008 | Dumange et al. |
| 7,784,937 B2 | 8/2010 | Keane et al. |
| 7,840,444 B2 | 11/2010 | Mellon et al. |
| 7,874,672 B2 | 1/2011 | Lieberman et al. |
| 8,002,406 B2 | 8/2011 | Arrigotti et al. |
| 8,020,990 B2 | 9/2011 | Keane et al. |
| 8,340,799 B2 | 12/2012 | Hagen et al. |
| 2002/0143653 A1 | 10/2002 | DiLena et al. |
| 2004/0004633 A1 | 1/2004 | Perry et al. |
| 2005/0021137 A1 | 1/2005 | Blake et al. |
| 2011/0299031 A1 | 12/2011 | Keane et al. |
| 2011/0301740 A1 | 12/2011 | Arrigotti et al. |
| 2011/0304816 A1 | 12/2011 | Arrigotti et al. |

OTHER PUBLICATIONS

"Aspheric Flat-Top 35," Product brochure of Bristol C & D, Inc., www.bcdlens.com, believed published before Aug. 10, 2010, 2 pgs.
"Bristolite Flat-Top," Product brochure of Bristol Consulting & Development, Inc., Miami, Fl., believed published before Aug. 10, 2010, 2 pgs.
"Cosmolit Aspheric Plus Lenses," Product brochure of Rodenstock GMBH, believed published before Aug. 10, 2010, 6 pgs.
Lenscrafters, http://www.lenscrafters.com, Apr. 24, 1999; pp. 1-8 [last accessed Sep. 26, 2002].
PCT International Search Report, Application No. PCT/US02/21610, Jan. 5, 2003, 3 pages.
PR Newswire, PlanetRx.com shows vision by adding contact lenses and eye care products to product mix, dated; Jan. 19, 2000, 3 pages.
"Single Vision Premium Lenses," Rodenstock GMBH, http://www.rodenstock.ca/index.php/product/item/12, downloaded Mar. 19, 2010, 1 pg.
"The Ultimate in Aspher," product brochure of Pentax Corporation (now division of Hoya Corporation of Japan), believed published before Aug. 10, 2010, 1 pg.
U.S. Appl. No. 60/303,361, filed Jul. 6, 2001, 48 pages.
U.S. Appl. No. 60/364,744, filed Mar. 15, 2002, 95 pages.

300A

305
```
TRAY   ACCT.      RX#       PATIENT   EYEF    POS INV.# 558534
6119   22608      22663647  GOLLI**********09/10/09  04:47P
DYER VISION CENTER, INC.         :816-331-9590 V     @@ 6F
BILL: 89551                      *REP*07/23SUTHERLIN OPTICA
```

310

| POLY | | −0.75 | BRIDGE DIST | | NEAR EPx | | 0.25@ −90 | |
|---|---|---|---|---|---|---|---|---|
| R | 0.00 | −0.75 | 110 | 32.0 | 29.5 | | | |
| | SPHERE | CYL | AXIS | 64.0 | 59.0 | | Δ IN/OUT | Δ UP/DN |
| L | −0.25 | −1.00 | 75 | 32.0 | 29.5 | | | |
| | | −1.25 | HORZ TOL → | 3.5 | VERT TOL → | | 0.25@ −90 | |

315

| R | 2.5 | 2.5 | 14.0 | 18.0 | | 1.9 | 2.6 | 2.1 |
|---|---|---|---|---|---|---|---|---|
| | DEC | INSET | OC HEIGHT | SEG HEIGHT | | THINNEST | THICKEST | CTR THICK |
| L | 2.5 | 2.5 | 14.0 | 18.0 | | 1.9 | 2.8 | 2.1 |

```
D05                       LENS STOCK
```

320

| S | VX ELLIPSE | | VX 80 | CLR | | 4.00 | 200 | ELIP |
|---|---|---|---|---|---|---|---|---|
| | STYLE | PLY/PLY | MFR SZ | COLOR | COAT | FRONT CURVE | ADD | |
| S | VX ELLIPSE | | VX 80 | CLR | | 4.00 | 200 | ELIP |

```
D05                        FRAME
```

325
```
 S   MOUNT I              5 GUNMETAL         TUSC
 o  SK  50 19 145  SKUL      ST  METL
     DATBASE PATT NO G CH
                     SURFACING
```

| R | B | 2.5 | +4.0 | 110 | 222 | | 58 | 64 | 4.04 | 0.382 |
|---|---|---|---|---|---|---|---|---|---|---|
| | GRIND | IN | DOWN | CYL AXIS | Δ AXIS | | BLOCK | CRIB | TRUE CURVE | SAG |
| L | B | 2.5 | +4.0 | 75 | 337 | | 58 | 64 | 4.04 | 0.382 |

330

| R | 0.14 | −4.09 | −4.78 | 6.1 | 15.7 | 8.5^ | | 2.8 | 2.1 |
|---|---|---|---|---|---|---|---|---|---|
| | BLOCK Δ | GEN BASE | GEN CROSS | GEN FRONT | GEN TK | BTHK | | Δ APEX | Δ BASE |
| L | 0.24 | −4.28 | −5.18 | 6.0 | 15.4 | 8.5^ | | 3.2 | 3.0 |

| R | −4.10 | −4.80 | 0.70 | | 1.54 | 1.80 | 6.1 | 12.1 |
|---|---|---|---|---|---|---|---|---|
| | TOOL BASE | TOOL CROSS | TOTAL CYL | | BASE SAG | CROSS SAG | TVAL | SVAL |
| L | −4.30 | −5.20 | 0.90 | | 1.61 | 1.95 | 6.0 | 12.1 |

```
    EQUITHIN   0.25s      POLYCARB POLISHED EDGE @ N/C
                           FRAME SUPPLIED
```

335
```
ALWAYS ROLL & POLISH HI INDEX    FINISHING      CITY 105
```

| R | 2.5 | P +3.0+ | 18.0 | | 13.5 | DBL | 19.0 |
|---|---|---|---|---|---|---|---|
| | INSET | DOWN | SEG HEIGHT | | CLEAR | ED | 52.3/022 |
| L | 2.5 | P +3.0+ | 18.0 | | 13.5 | FPD | 69.1 |
| | SET | POLISH METL | PATTERN d | CIRC | OVER PBOX | HORZ | VERT |
| 36.3 | RIMLESS DRILL 4 | | S5127 | 137.6 | −0.1  50.3 | 50.1 | 30.3 |
| | TINT | | | | COAT | | CXS |

```
                          CLARION XS
```

EYEN                    BILLING FOR CHEM CLIP IN GRY ON A SEP
                            INV

AUTOMATED OPTICAL LENS PROCESSING SYSTEM, SUCH AS A SYSTEM FOR PROVIDING SUPPLEMENTAL INFORMATION TO LABORATORY TECHNICIANS

CROSS-REFERENCE TO RELATED APPLICATIONS

This application is a continuation of U.S. patent application Ser. No. 12/644,454, filed Dec. 22, 2009, which is hereby fully incorporated by reference. This application relates to U.S. application Ser. No. 10/483,113, now U.S. Pat. No. 7,188,082, which is hereby fully incorporated by reference.

BACKGROUND

Eyeglass prescription orders are typically accomplished by filling out a form that requires completing an average minimum of 20 discrete blanks or fields and may have up to 75 fields or more depending on the special requirements of the order. The information contained in an eyeglass prescription order can be classified into the following several groups.

Two key items in the order are: the actual prescription—A patient's refractive powers; and Patient information—Name, plus the measurements of the patient's eyes horizontally and vertically with respect to the patient's chosen frame.

The Frame—Since most frame companies sell directly to Eye Care Professionals (ECPs), the frame is frequently enclosed with the prescription ("Rx") or sent later to an optical laboratory to process lenses for the frame. The frame must be described on the order, even if not supplied, because the laboratory must be able to identify customer frames if separated from the lenses in the lens production process.

Lens Product—There are hundreds of different types of lens styles, each one may come in different materials (glass, plastic, etc.), and each material may come in different colors, coatings, and power combinations. A frequent error in eyeglass prescription ordering is specifying an unavailable lens product. That is, each separate piece of information of the lens order is valid, but taken together describes a product or lens that either is not made or is not available from the laboratory that received the order.

Lens services—There are a variety of lab-supplied services that can be added to a lens product as described above. For example, labs often provide coatings for scratch resistance, anti-reflection, mirror-reflection, or colors. Order options should be available for selected lens products and compatible.

Another type of lens service provided by labs relates to edging processes (shaping for insertion into frames). A lens may be polished on the edge or ordered to a specific thickness. Again, errors in ordering occur because certain finishing features may not be available for the particular lens/frame combination selected.

All the various components of an eyeglass prescription order may indeed make sense when viewed independently, but there is an error rate of more than 20% associated with handling orders that result from incompatibility in the "inter-relationships" between the items on the order, thus making the order not manufacturable in the laboratory by the technician.

The need exists for a system that overcomes the above problems, as well as one that provides additional benefits. Overall, the examples herein of some prior or related systems and their associated limitations are intended to be illustrative and not exclusive. Other limitations of existing or prior systems will become apparent to those of skill in the art upon reading the following Detailed Description.

BRIEF DESCRIPTION OF THE DRAWINGS

FIG. 3A is an example work ticket where lens processing parameters are displayed on a form.

FIGS. 5A-5D are work ticket forms showing examples of tool tips that provide supplemental information for lens processing.

DETAILED DESCRIPTION

Overview

Described in detail below is a system that can accept an eyeglass prescription and create a work ticket for use by a laboratory technician for manufacturing the prescription lenses. The process for creating the work ticket accepts machine settings for controlling lens manufacturing equipment, accesses data files for specific lens materials, and performs lens calculations to optimize thickness values of the lens. The information used by the system to create the work ticket can be accessed as supplemental information through the use of tool tips by a user of the work ticket. The work ticket is displayed on a screen to the user. When a user moves a cursor over the various fields of the work ticket, the system displays relevant supplemental information corresponding to the different fields. Tool tips are useful as a training tool for laboratory technicians, setting up new equipment used to manufacture eyeglass lenses, analyzing an eyeglass prescription job that is problematic to manufacture, etc.

Various aspects and examples of the invention will now be described. The following description provides specific details for a thorough understanding and enabling description of these examples. One skilled in the art will understand, however, that the invention may be practiced without many of these details. Additionally, some well-known structures or functions may not be shown or described in detail, so as to avoid unnecessarily obscuring the relevant description.

The terminology used in the description presented below is intended to be interpreted in its broadest reasonable manner, even though it is being used in conjunction with a detailed description of certain specific examples of the invention. Certain terms may even be emphasized below; however, any terminology intended to be interpreted in any restricted manner will be overtly and specifically defined as such in this Detailed Description section.

Figure 1:
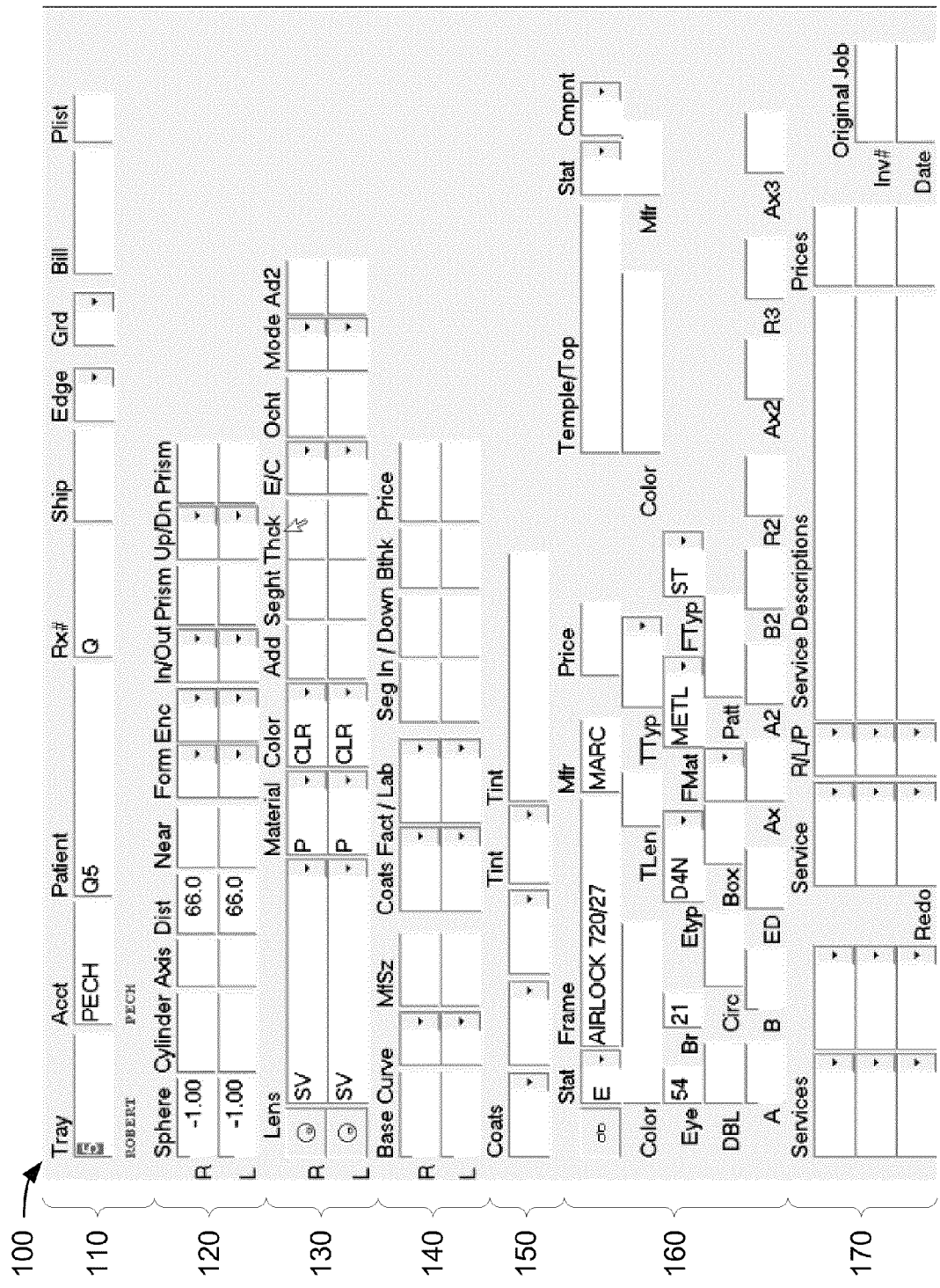
FIG. 1 shows an example of a prior art eyeglass lens prescription entry form.

FIG. 1 shows an example of a prior art prescription lens entry form for an electronic ordering system used by an eye care professional (ECP), as described in U.S. Pat. No. 7,188,082 and is incorporated herein by reference. Information used to identify the patient and the ECP are provided in section 110. The prescription for the eyeglass lenses is entered in section 120. Prescription information includes, but is not limited to, spherical power, cylindrical power, and cylindrical axis of each lens ordered.

At section 130, specific information about the lenses, for example, the style of the lens (single vision, bifocal, etc.), lens material (polycarbonate, glass, etc.) and lens color or tinting, can be specified. Further information about customizing the lenses to the patient's preferences, such as lens coatings, can be entered in sections 140 and 150. Section 160 allows the ECP to enter information about the patient's chosen frames. And section 170 provides pricing and other customized services requested by the ECP and/or the patient.

The prescription lens information can be entered directly into an electronic eyeglass or lens ordering system by the ECP and then exported to a different electronic lens processing system. Alternatively, the prescription can be entered manually into an appropriate lens processing system by data entry personnel. Once the prescription information is made available to the processing system, the system takes the eyeglass ordering information and generates a work ticket to be used by the optical laboratory technician to manufacture a custom pair of eyeglasses that meet the prescription requirements.

Suitable Processes and Interfaces

Figure 2A:
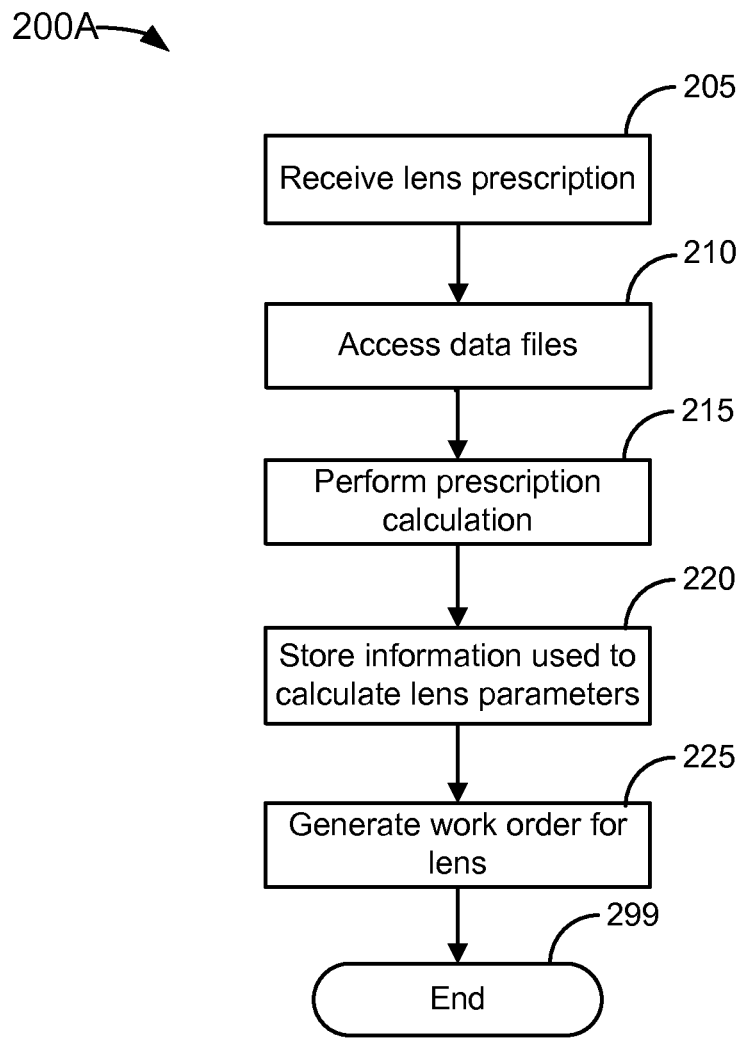
FIG. 2A is a flow chart illustrating an example of a method of generating a work ticket from a lens prescription.

FIG. 2A is a flow chart illustrating an example of a method 200A of generating a work ticket for manufacturing the lenses for an eyeglass prescription. At block 205, the system receives a lens prescription that has been ordered by an ECP. The lens prescription can include, but is not limited to, information shown in the example prescription entry form shown in FIG. 1.

At block 210, the system accesses data files to perform lens layout calculations and determine appropriate lens tool settings for manufacturing the custom lenses. Examples of accessed data files include, but are not limited to, lens stock data, frame stock data, surfacing data, finishing data, and other miscellaneous data files. Examples of lens stock data include style attributes, such as minimum fitting height for progressive lenses; material attributes, such as tintability and compatibility with various coatings; recommended lens base curve selection information for use with particular eyeglass prescriptions; lens technical information, such as lens blank dimensions and curve measurements; lens inventory in the laboratory; and lens pick lists for which manufacturer's lens blank and which lens size to use for a given prescription, ranked according to the laboratory's preferences. Examples of frame stock data includes size and color availability; whether a frame is available for requested eye, bridge, and/or temple measurements; and technical details, such as the minimum lens edge thickness and compatible lens base curve. Examples of surfacing data include setup files for the generator, i.e. surfacing machine; prism data that tells how much prism the generator is capable of producing in a generated lens; information about the dimensions of the blocks used to hold the lenses in the generator; information about the tools the generator uses to grind lenses and the pads placed on the tools, such as the diameter and curvature of the tools and thickness of the pads; and gauge data that provides the type of gauge used to measure the lens curves and thicknesses. Examples of finish data include whether a coating is compatible with a particular tint or lens material; adjustments made to the prescription to account for the way the frame fits on a patient's face; and the position and shape of drill holes. Examples of other data files include information that flags preferences or warnings that are specific to a particular account and/or doctor, such as a doctor specifying an anti-reflective coating on every order.

In one example where data files need to be accessed, a lens manufacturing tool called a lap is used. The lap tool has a particular curve and is covered with abrasive pads of various types and thicknesses that grind a lens blank of a chosen material to alter the curvature of the lens blank to produce the desired lens geometry. Lap tools are available in different increments and with certain calibration values. A typical eyeglass manufacturing facility has an inventory of approximately 6000 lap tools. For each prescription, the optimum lap tools should be chosen that are most suitable for creating a lens for that prescription. Consequently, information related to the lap tools used by a particular laboratory should be accessible by the system to select appropriate tool settings during the lens processing calculations. Because the pads, the tool increments, and the way the tools are cut all impact the selection of the lap tools for a particular job, it can be beneficial for a laboratory technician to be able to access the selection information through the tool tip system. The supplemental information provided through tool tips not only allows the laboratory technician to check the tool, but also to learn why the system selected certain tools and parameters for the manufacturing process.

Then at block 215, the system uses the data in the files accessed at block 210 to perform a prescription calculation for generating the prescribed lens. Input information for the lens calculations includes, but is not limited to, the lens prescription order information and the frame information, such as the shape of the frame, and the other data files listed above. One calculation selects the appropriate lens based upon data such as the patient's measurements, the power of the patient's prescription, and set up files for the generator for the particular laboratory. Another calculation involves calculating the cosmetics of the job based upon data such as the frame, the lens, the prescription, and calculating the thickness over the entire lens. Similarly, all of the surfacing, fining, and polishing information for a lens require calculations by the system Thus, information generated by the calculation includes, but is not limited to, the specific lens tools to be used such as the lap tools and blocks to be used during the lens manufacturing process, calculations of the final thickness of the lens over the entire lens surface, and the work ticket calculations for surfacing and finishing the lens.

At block 220, the system stores information used during the lens calculation to generate the prescribed lens. In one embodiment, not all of the information and calculations generated by the system during the prescription calculations need to be stored, only enough information needed to re-calculate any supplemental information needed by the lab technician when requested with tool tips. Alternatively, the system can store all the values and parameters determined during the prescription calculations as supplemental information for display when requested through tool tips. The laboratory technician can access the stored information during processing of the lens as needed, using the intuitive user interface provided by the tool tips to be described below.

At block 225, the system generates a work order or work ticket for the lens. The work ticket can include a form showing the lens manufacturing parameters and/or a graphic of the lens blanks to be machined into the final prescription lens. The work ticket is referenced during the lens manufacturing process by the technician who will be making the custom lens. One example of a work ticket 300A is shown in FIG. 3A. The process ends at block 299.

Figure 2B:
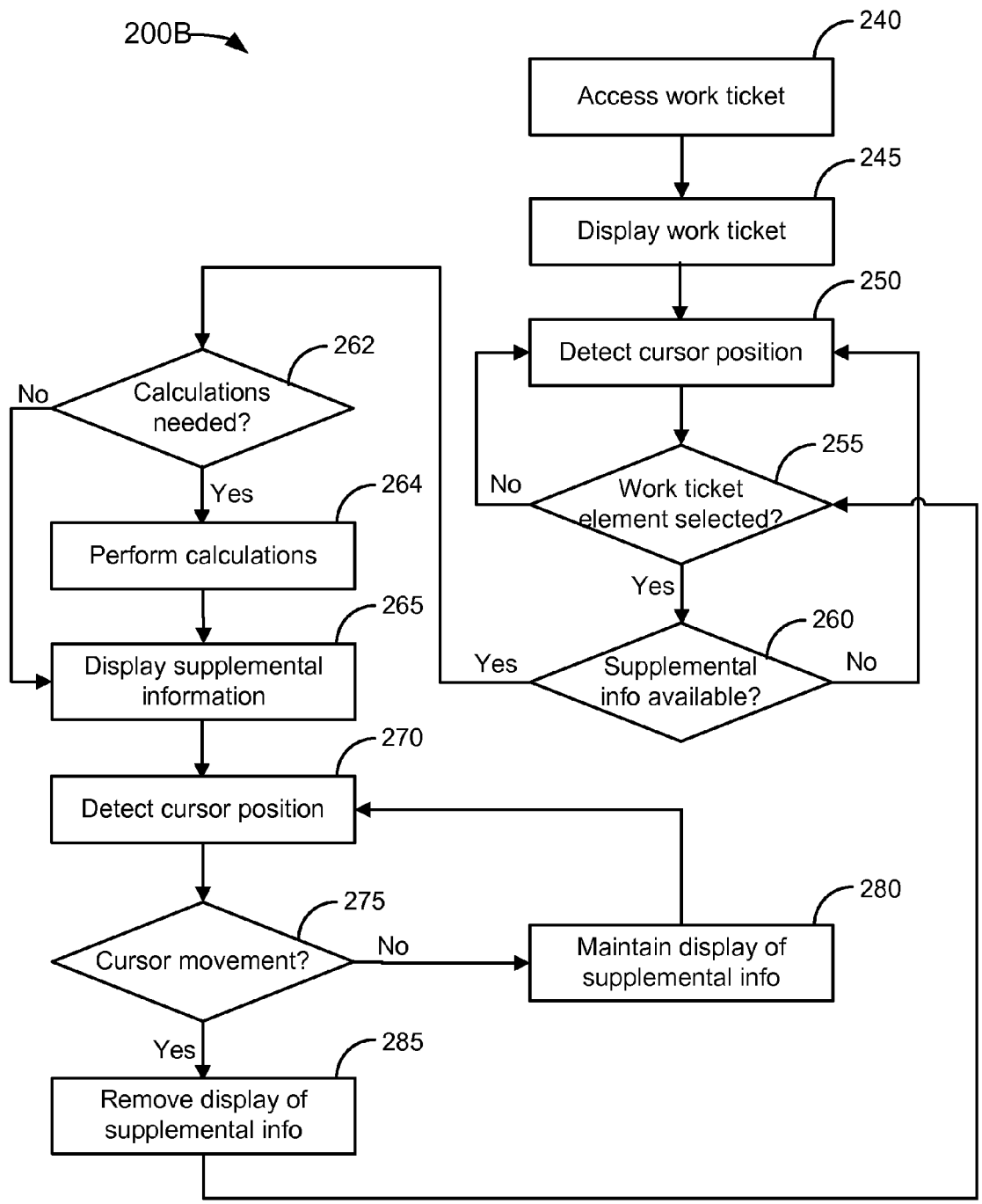
FIG. 2B is a flow chart illustrating an example of a method of displaying supplemental information for a work ticket on a display.

FIG. 2B is a flow chart illustrating an example of a method 200B of displaying supplemental information for a work ticket on a display.

At block 240, the system accesses the work ticket generated at block 225 of FIG. 2A. The system accessing the work ticket at block 240 may or may not be the same as the system that generated the work ticket. The work ticket can have the format of a form, for example the form 300A shown below in FIG. 3A. Additionally or alternatively, the work ticket can have a graphical format, for example the graphic 300B shown below in FIG. 3B. The graphic is a picture of the lens or lenses 350, 352 to be manufactured superimposed on the lens blank 355 to be used. The system then displays the work ticket on a screen at block 245.

The screen should be remotely accessible by a user through the use of an input device, such as a mouse, to move a cursor over the work ticket displayed on the screen to select elements of interest from the work ticket to obtain supplemental information. Supplemental information can include standard documentation about the item of interest. Alternatively or additionally, supplemental information can include customized lens parameter values that have been used in a prescription lens calculation for the lens, for example, the refractive index of the lens material used in the calculation, the minimum thickness of the lens, the effect of polishing on the thickness of the lens, and/or gauge parameters to be used for measuring lens sag during or after the manufacturing process.

Movements of the cursor on the display made by the user are detected by the system at block 250. Then at decision block 255, the system determines whether a work ticket element has been selected by the user. A user can select an element by moving the cursor to or near an element. If the cursor has not been moved or has not been moved to or near an element that has supplemental information associated with it (block 255—No), the process returns to block 250. If the cursor has been moved to or near an element of the work ticket (block 255—Yes), the process continues to decision block 260.

At decision block 260, the system accesses a work element database to determine whether there is any supplemental information available for the selected element of the work ticket. If there is no supplemental information available (block 260—No), the process returns to block 250. If there is supplemental information available (block 260—Yes), the process continues to decision block 262 where the system determines if any calculations need to be performed to find the appropriate parameters, values, and other information to be displayed in tool tips.

If calculations are needed (block 262—Yes), the system performs the requisite calculations at block 264, and the process continues to block 265. If no calculations are needed (block 262—No), the process continues to block 265 where the system displays the appropriate supplemental information. The supplemental information can include, but is not limited to, calculations, parameters, steps used by the system to derive the parameters, and/or documentation, and the supplemental information can be provided in different formats, for example as a pop-up tool tip box, or as a separate window.

At block 270, the system again detects the position of the cursor on the screen. Then at decision block 275, the system decides whether there has been any movement of the cursor. If the cursor has not moved (block 275—No), at block 280 the system maintains the display of the previously accessed supplemental information on the screen, and the process returns to block 270. If the user has moved the cursor (block 275—Yes), the system can remove the display of supplemental information from the screen at block 285. Then the process returns to decision block 255 to decide whether another work ticket element has been selected.

FIG. 3A is an example work ticket where lens manufacturing instructions and parameters are displayed on a form 300A. The work ticket has several sections. Any of the work ticket calculations in any section of the work ticket may be selected by the user to obtain additional relevant related lens processing information stored by the system. The identification and contact information for the patient and/or the ECP are displayed in section 305, and the lens prescription information provided by the ECP is shown in section 310.

The lens information that describes the parts to be selected from inventory for manufacturing the lens are shown in section 320. Lens information includes the lens manufacturer, size of the lens, whether the required lens type is stocked, and the type of lens, for example, single vision, progressive, plastic, high index, polycarbonate, coated, or uncoated. The frame information for the eyeglasses is shown in section 325, for example, the style, color, and manufacturer, and whether the frame has a rim or is rimless.

Information relating to surfacing of the lens is displayed in section 330. The first line in section 330 provides information for laying the lens out for blocking and applying the block. The second line in section 330 provides information on how to set the generator, including the amount of prism needed, the base curve which creates the spherical power of the lens, and the cross curve which creates the cylindrical or astigmatic power of the lens. Prism can be induced in lenses for many reasons, for example, if the doctor prescribes a prism to be placed in front of the patient's optical center, by tilting the lens and inducing a prism, the optical center can be moved around on the lens. Sometimes the laboratory equipment requires that the prism is created at the blocker by tilting the holding device, other times the machine that cuts the curves on the back of the lens offsets and creates the prism. Also, a laboratory might have a different piece of equipment for processing a polycarbonate lens than for processing a glass lens or lens made of another material. Thus, the tool tip allows a laboratory technician to select the prism entry on the work ticket to see how the equipment is set up for a particular lens manufacturing job without having to reference a setup file that changes for different lenses.

The base and cross curves specified in the second line in section 330 are the curves to be cut into the lens by the generator. The third line in section 330 provides information on the tools used to produce the base and cross curves. The set of tool curves specifies the lap tools that are used to polish out the curves that are cut by the generator. Essentially, pads made of sandpaper are used to remove the rough marks of the machines that cut the curves and to produce an optical quality surface. Consequently, there is a difference between the first set of machine tool curves specified in the second line and the second set of surface curves specified in the third line that are created by the tool.

The surfacing information given in the second line of section 330 further includes the settings for the grinding machine that selects the thickness of the lens to be ground. The information in the second line provides the thickness of the blank and further shows calculational caliper checks that can be used to determine whether the edge of the surfaced lens has the correct thickness. Because different machines have different setup methods and different thickness settings that are particular to the type of generator being used by the laboratory, the tool tip system can conveniently show a setting value that is different from the actual final thickness of the lens to be produced.

Further, the third line of section 330 provides base sag and cross sag parameters that are used by gauge measuring tools to ensure that the curves are cut the way the system calculates that the curves should be cut. A user can access the information using the tool tip by moving a cursor over the appropriate work ticket element, causing the information to be displayed in a pop-up box. Thus, if the machine setting is not needed by the user, the additional information does not clutter up the work ticket.

Surfacing information can also include the technical details required to produce the appropriate curves on the selected lens blank, for example, the layout method, the reference point for the particular lens style, the lap tool precision and the lap tool pad thickness used in the lens calculation. These parameters are used by the laboratory technician to produce the lens and to check that the correct machines in the laboratory are used to produce the appropriate lens prescription. Thus, the tool tips can be used for proofing operations and for setting up a new piece of equipment in the laboratory.

Information relating to finishing of the lenses is displayed in section 335. The finishing information includes, but is not limited to, rolling the edges of the lens, polishing the lens, coating the lens, and tinting the lens.

For prescriptions that specify rimless frames, information on drilling of holes in the lens is needed. The holes have certain geometric requirements because a lens must have a minimum thickness to hold the mounting apparatus for the frame. The lens also has a maximum thickness imposed by the drilling equipment. Thus, the tool tip can provide information on drill-hole thicknesses in the lens. If the drill-hole thickness is not within an acceptable range, the prescription can be flagged as a problem. The drill-hole thickness information can be visualized using the tool tip functionality with the graphical work ticket described below in FIG. 3B.

Figure 3B:
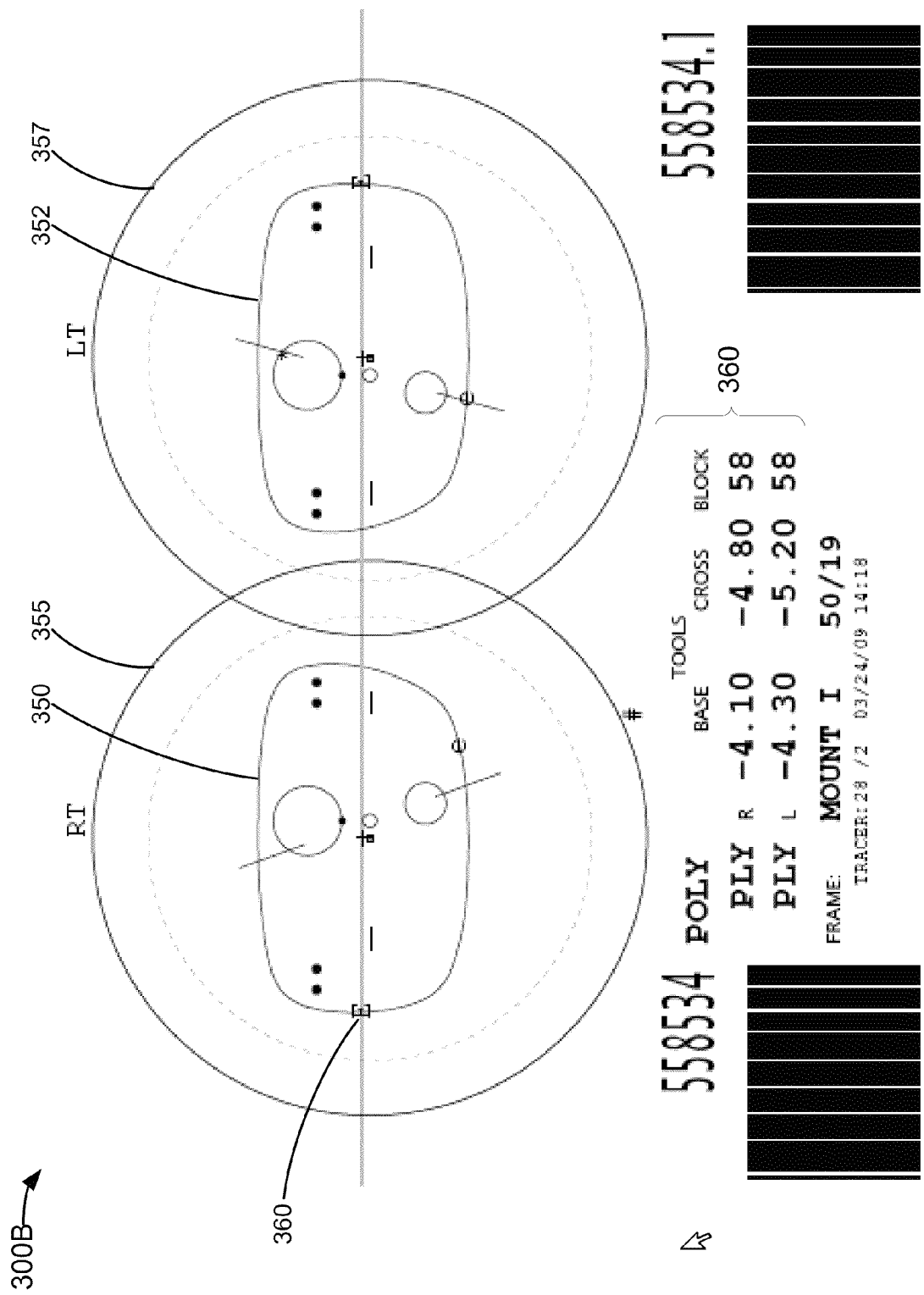
FIG. 3B is an example work ticket showing lens processing parameters displayed in a graphical format.

FIG. 3B is an example work ticket showing cosmetic information about the lens manufacturing parameters displayed in a graphical format 300B. The work ticket graphic 300B shows the patient's right lens 350 on the left and the patient's left lens 352 on the right, the way the patient's lenses would be seen on the patient's face. The lenses are superimposed on images of the starting round lens blanks 355, 357 from which the lenses will be manufactured.

Also shown in the graphic 330B are some markings used by lens blank manufacturers. Because different lens blank manufacturers use different markings, it would be helpful for the lens technician to have a readily accessible definition of the markings available through the use of tool tips. Thus, if the technician making the lens points a cursor at one of the markings, the system can be programmed to display the meaning of the marking in a tool tip and any specific effects the marking will have on the lens being manufactured. For example, the letter "E" marking 360 as shown in FIG. 3B identifies the thickest point on the periphery of the lens to be manufactured. The optimum thickness of the lens at a specific point selected by the cursor can also be displayed in a tool tip to aid the technician in manufacturing the lens.

Tool information for producing the lenses are displayed in section 360 below the graphics of the lenses.

Figure 4:
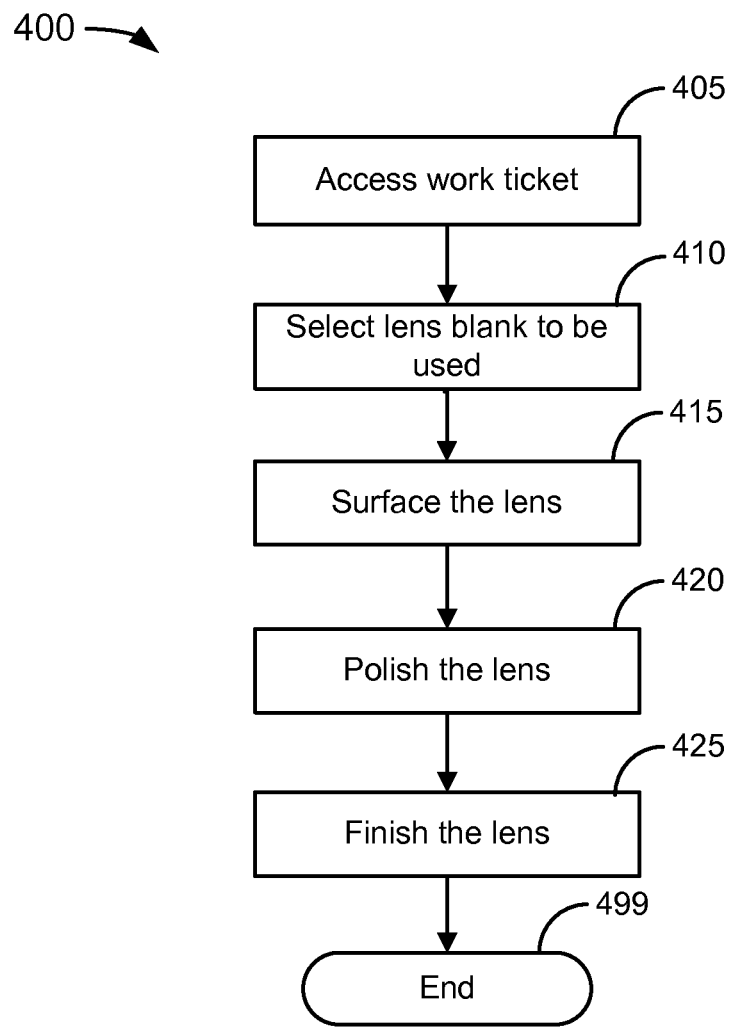
FIG. 4 is a flow chart illustrating an example of a method used by a laboratory technician to manufacture a lens according to a lens prescription.

FIG. 4 is a flow chart illustrating an example of a method 400 used by a lab technician to manufacture a lens according to a lens prescription. At block 405, the technician accesses the work ticket in form format, for example 300A in FIG. 3A, and/or graphical format, for example 300B in FIG. 3B, on an electronic display. Based upon the information provided in the work ticket, at block 410, the technician selects a lens blank having the appropriate parameters for manufacturing the lens, such as lens material, any requested lens tint, and polarization.

At block 415, the technician surfaces the lens based at least upon the information listed in section 330 of FIG. 3A. At blocks 420 and 425, the technician polishes and finishes the lens based at least upon the information listed in section 335 of FIG. 3A. Throughout the lens manufacturing process, the lab technician can access supplemental information using the tool tips to determine whether the lens is being manufactured according to the system's prescription calculation. The process ends at block 499.

Figure 5A:
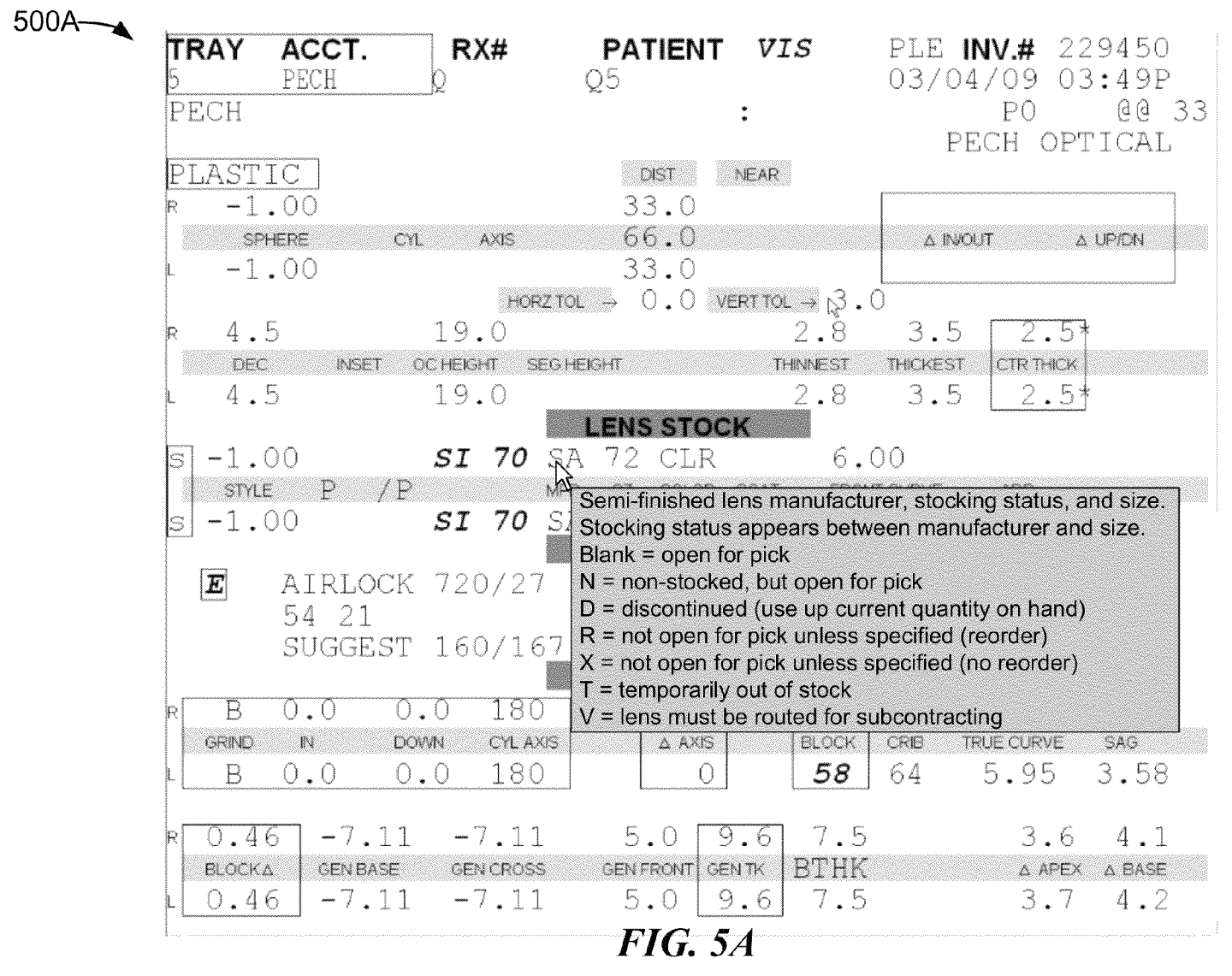
Figure 5B:
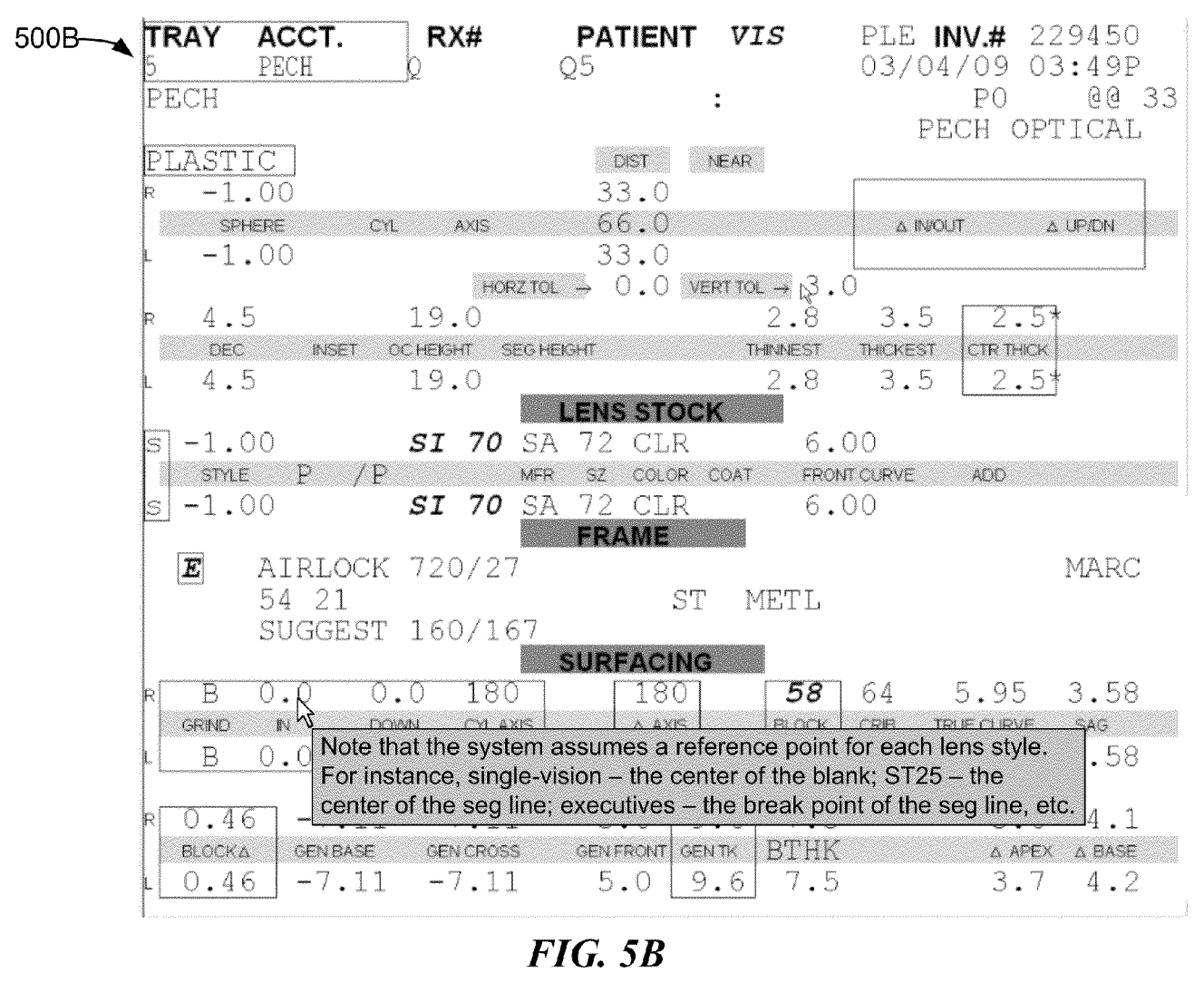

FIGS. 5A and 5B are examples of work ticket forms showing examples of tool tips that provide supplemental information that functions as documentation to more fully describe a field or a symbol shown on the work ticket. FIG. 5A shows the upper portion of the work ticket form shown in FIG. 3A with supplemental information provided in a tool tip about the lens manufacturer and the lens blank. FIG. 5B shows the upper portion of the work ticket form shown in FIG. 3A with supplemental information shown as a tool tip that discusses the reference point for a particular lens style. Documentation information is easily provided through the use of tool tips.

Figure 5C:
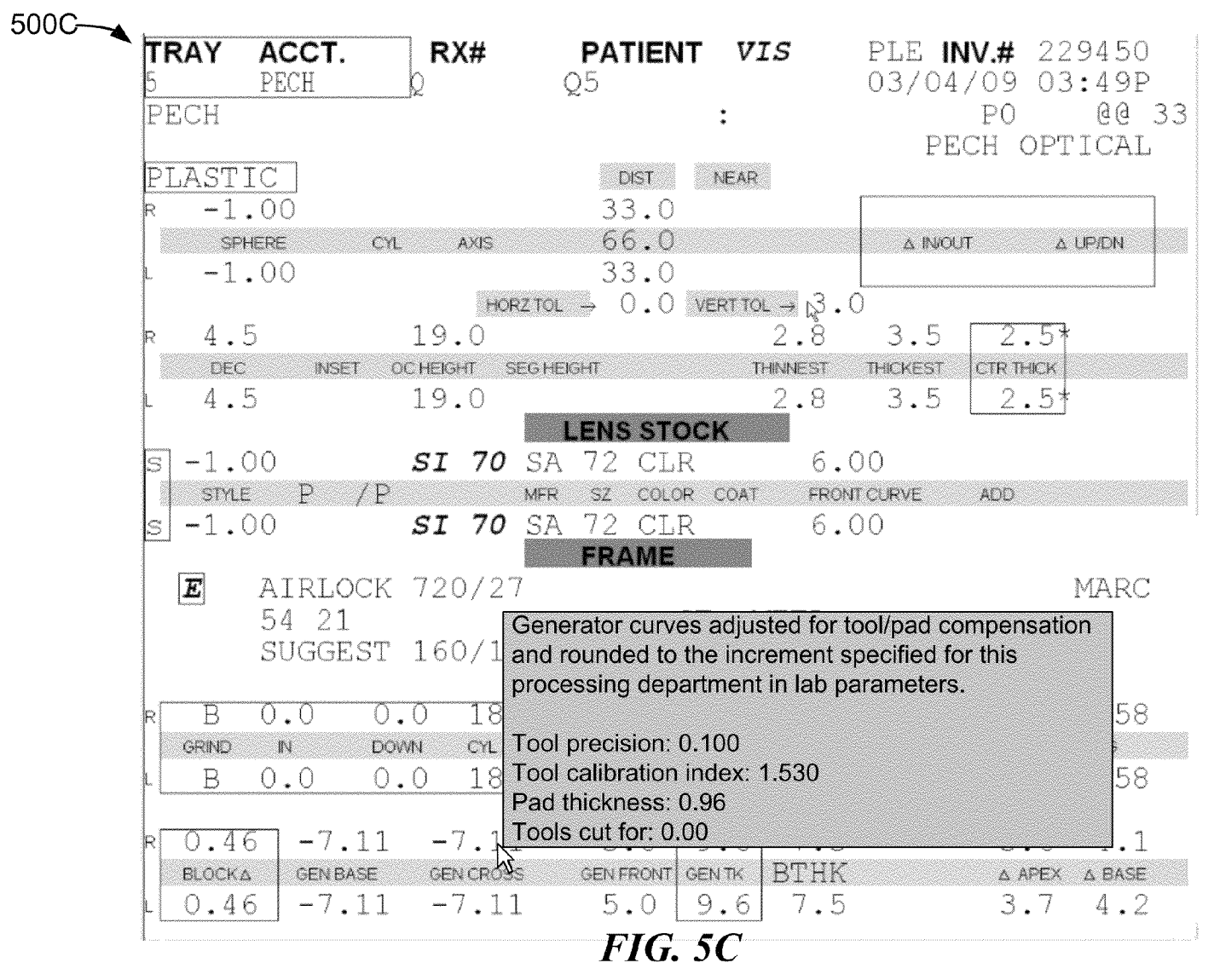
Figure 5D:
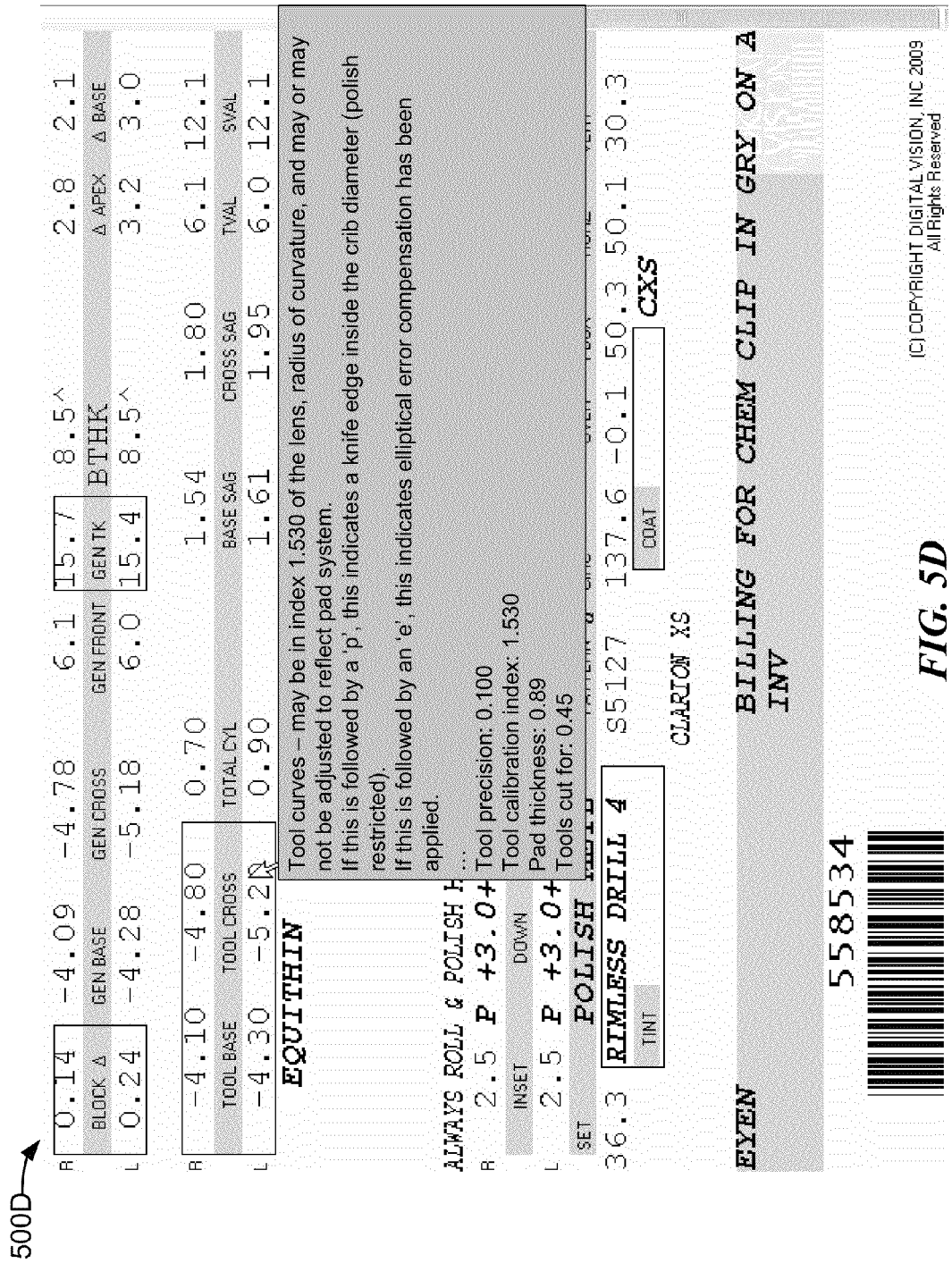

FIGS. 5C and 5D are examples of work ticket forms showing examples of tool tips that provide supplemental information where the supplemental information provides dynamic customized lens information useful to the lab technician for manufacturing a prescribed lens, determining why a prescription calculation does not yield a manufacturable lens, or ensuring that a lens satisfies the requirements of the job. FIG. 5C shows the upper portion of the work ticket form shown in FIG. 3A with supplemental information shown as a tool tip about generator curves that are adjusted for tool/pad compensation. Additionally, supplemental information is provided about the lens manufacturing tools used in the laboratory and taken into account by the lens calculation program when determining the work ticket calculations shown in the work ticket. FIG. 5D shows the lower portion of the work ticket form shown in FIG. 3A with supplemental information provided in a tool tip about the tool curves, such as the radius of curvature and tool precision information. Thus, the dynamic tool tip information can provide information on how particular parameters have been obtained, rather than just labeling or providing definitions of a given field or symbol.

Figure 6A:
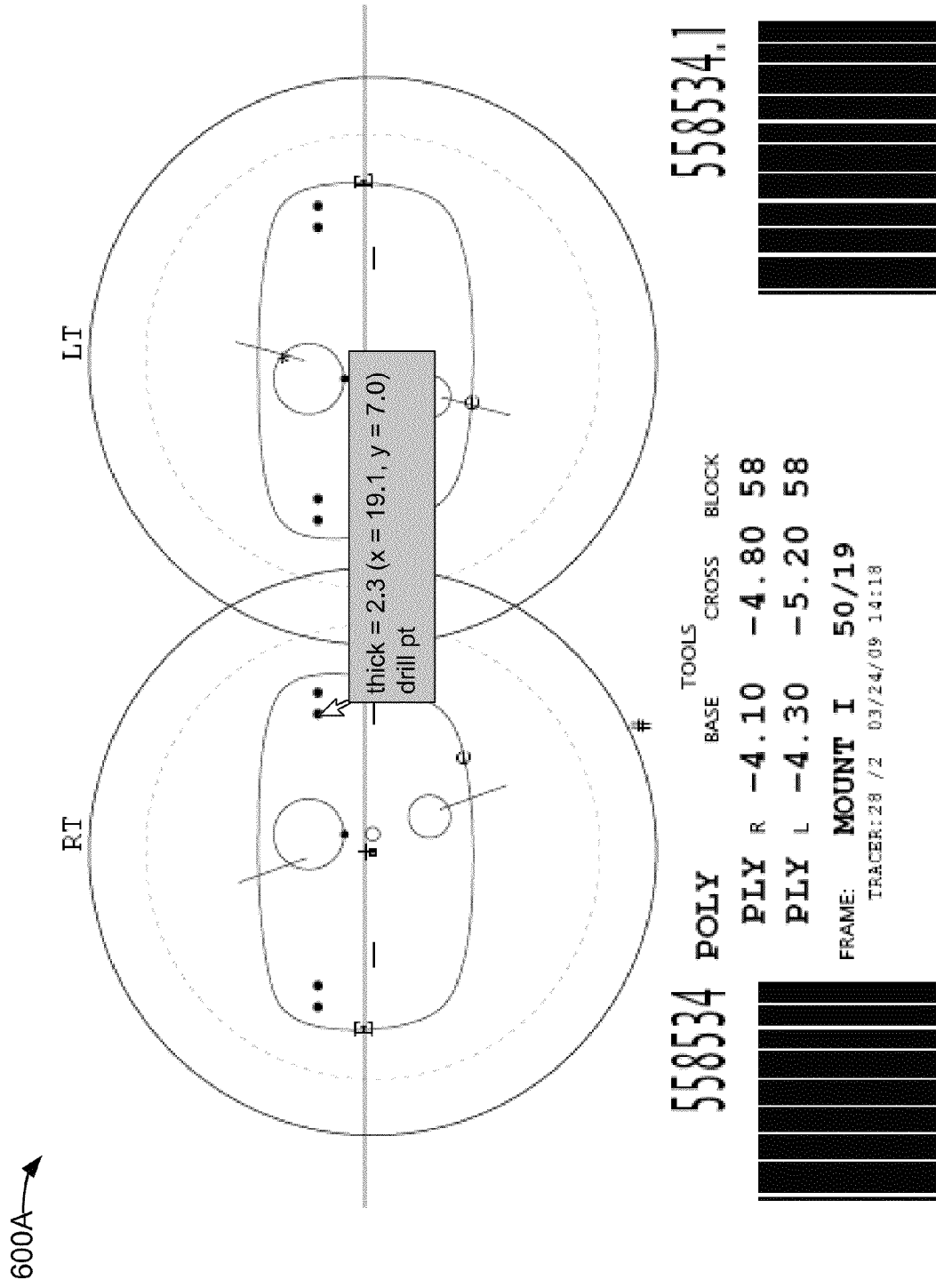
FIGS. 6A-6H are examples of graphical work tickets showing examples of tool tips that provide supplemental information for lens processing.
Figure 6B:
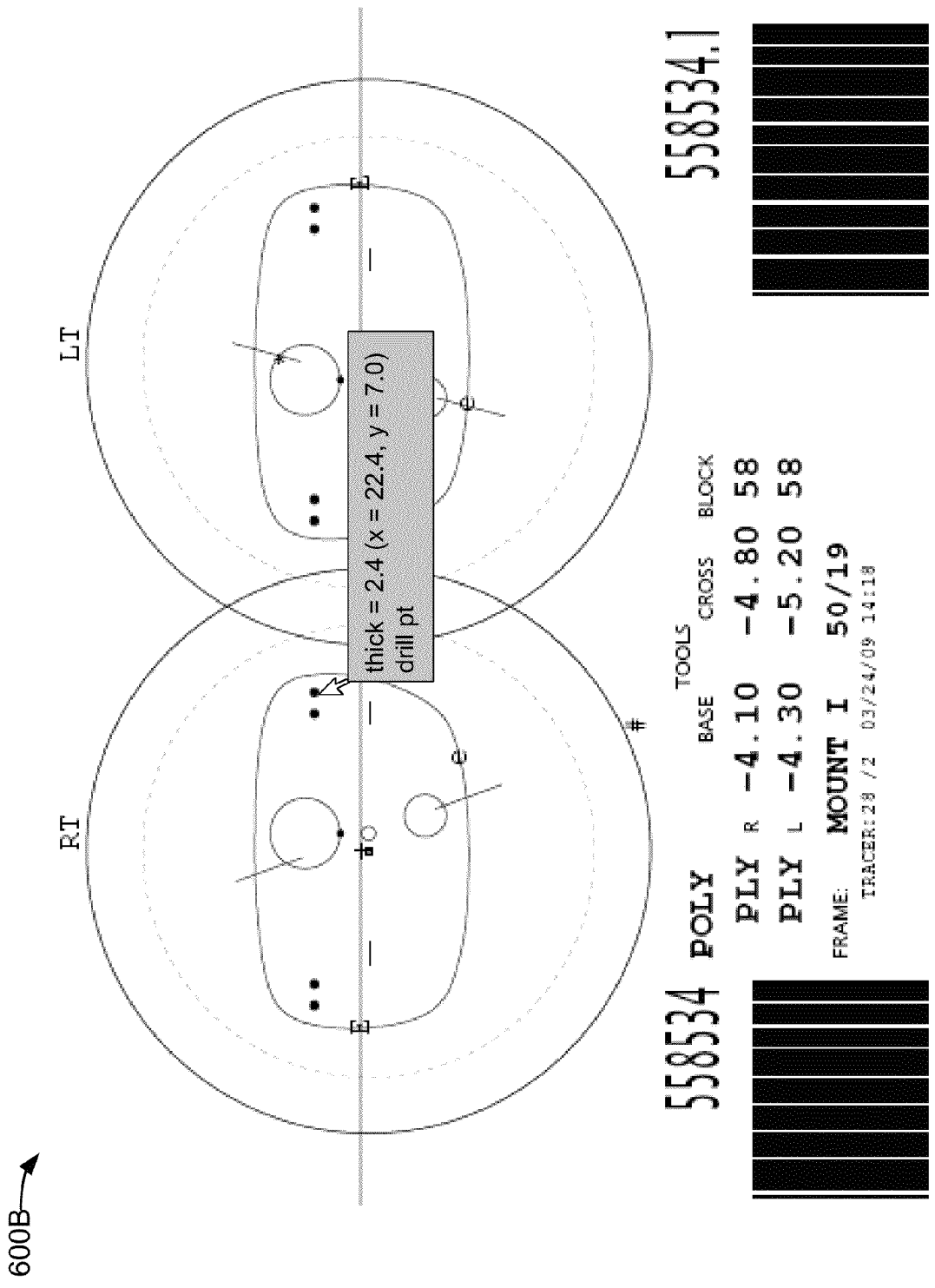
Figure 6C:
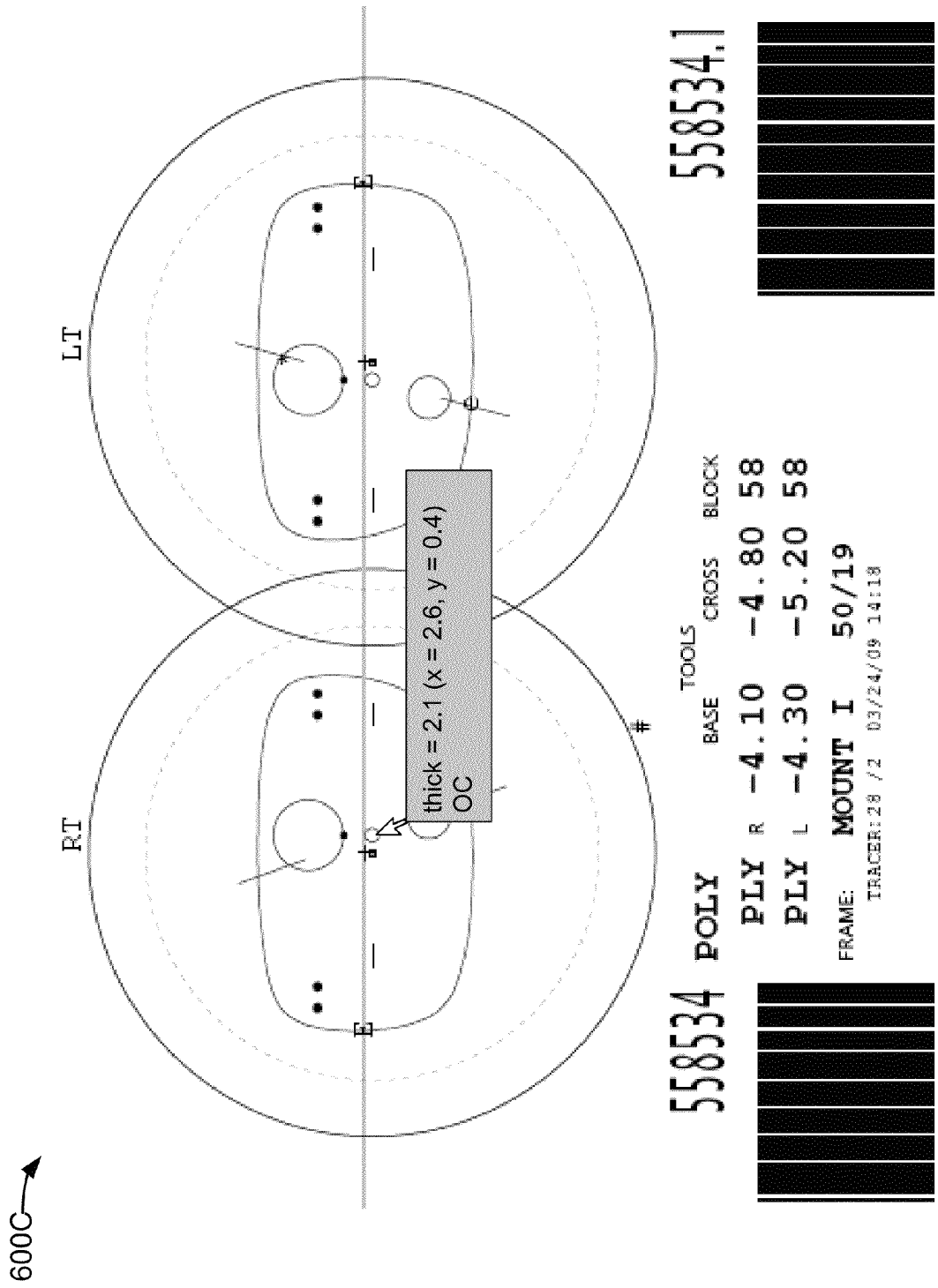
Figure 6D:
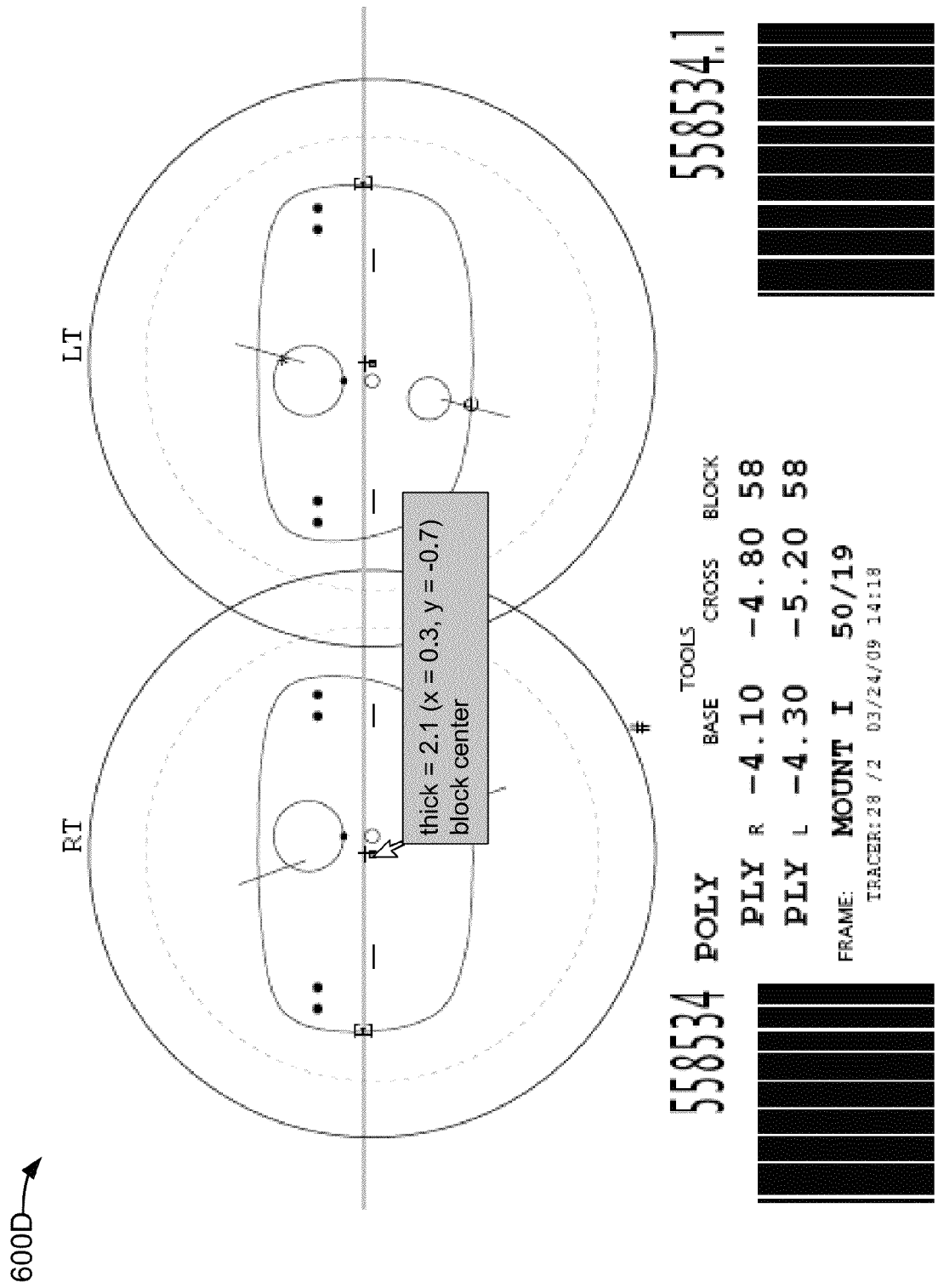
Figure 6E:
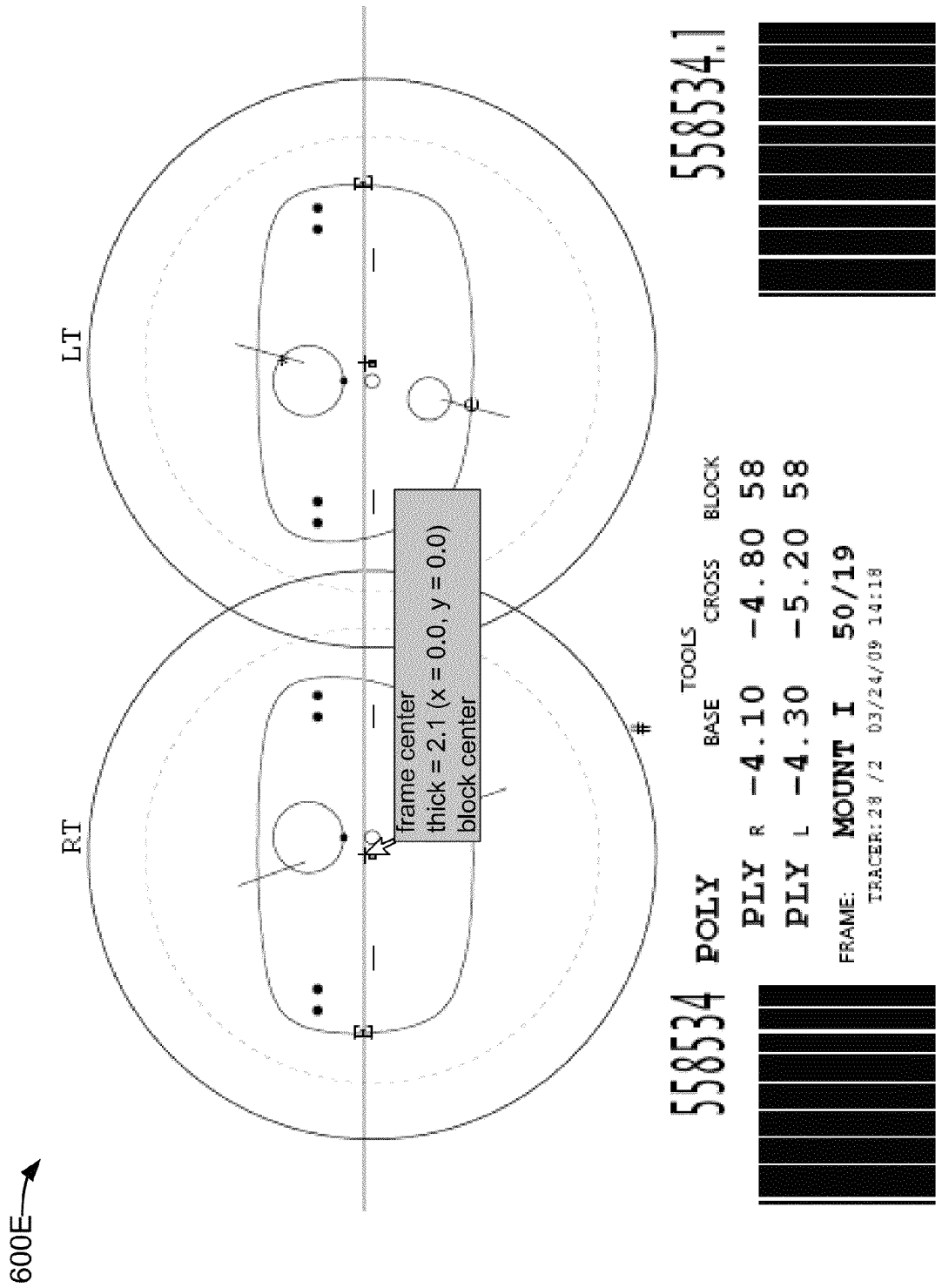
Figure 6F:
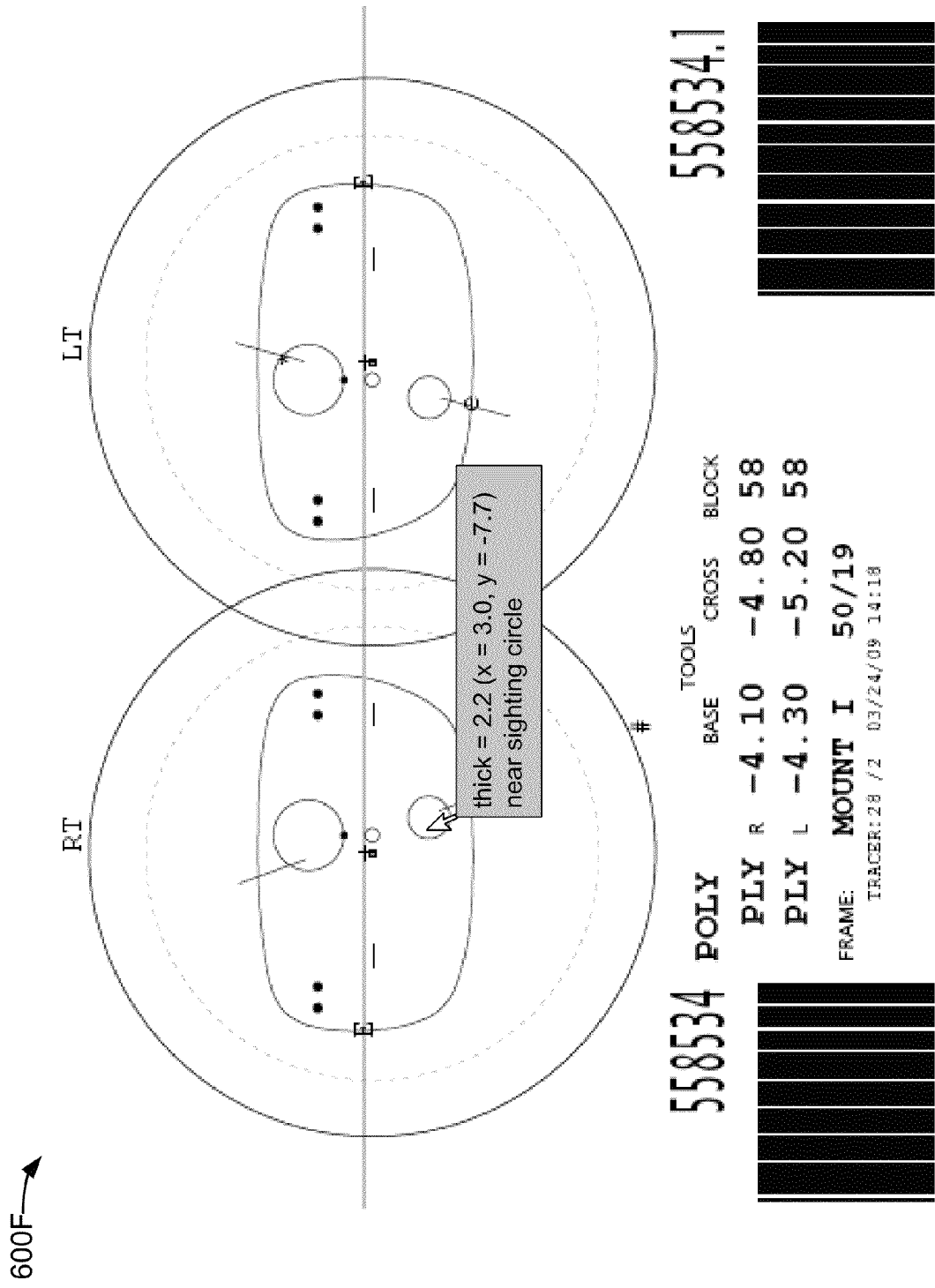
Figure 6G:
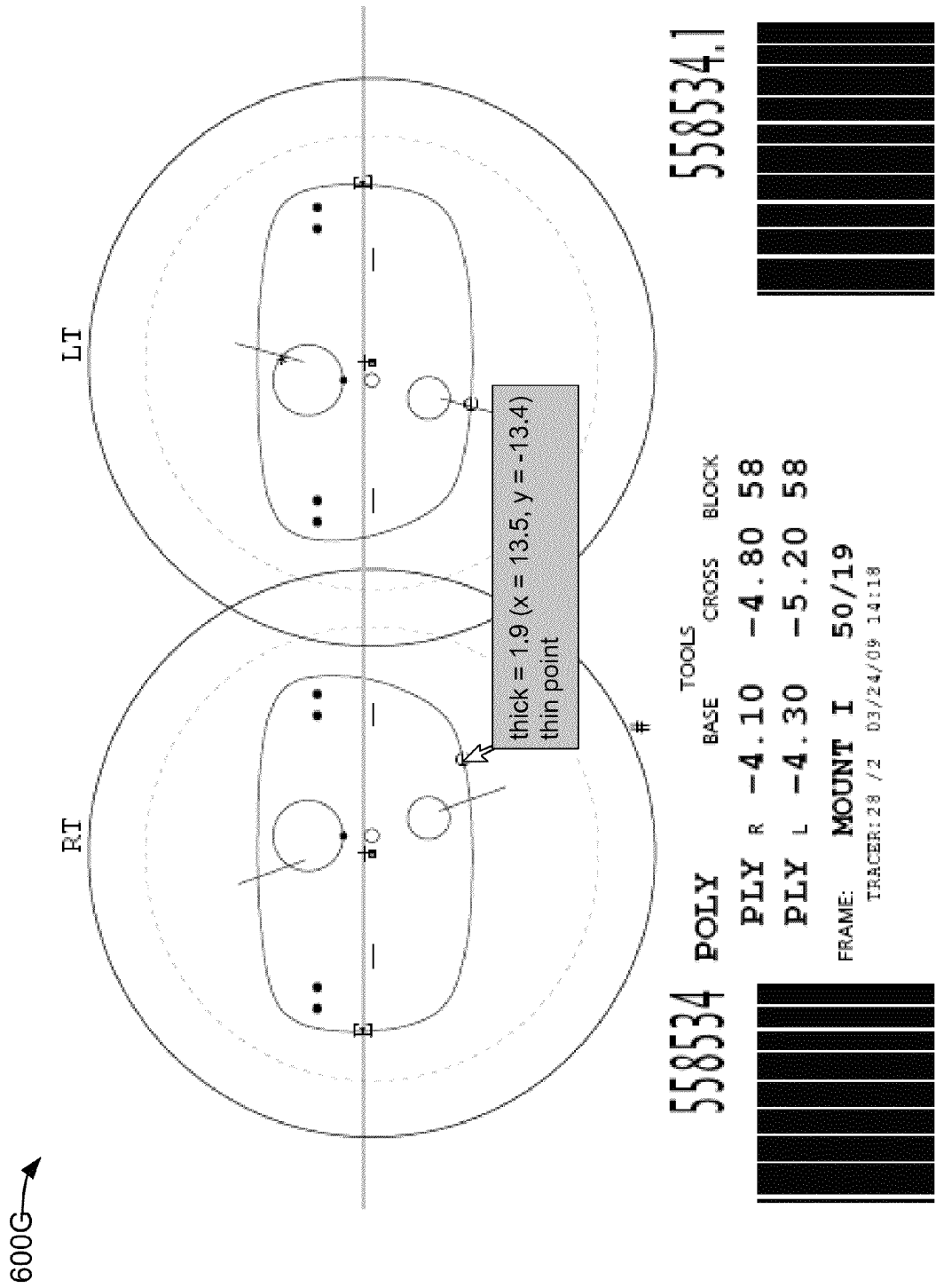
Figure 6H:
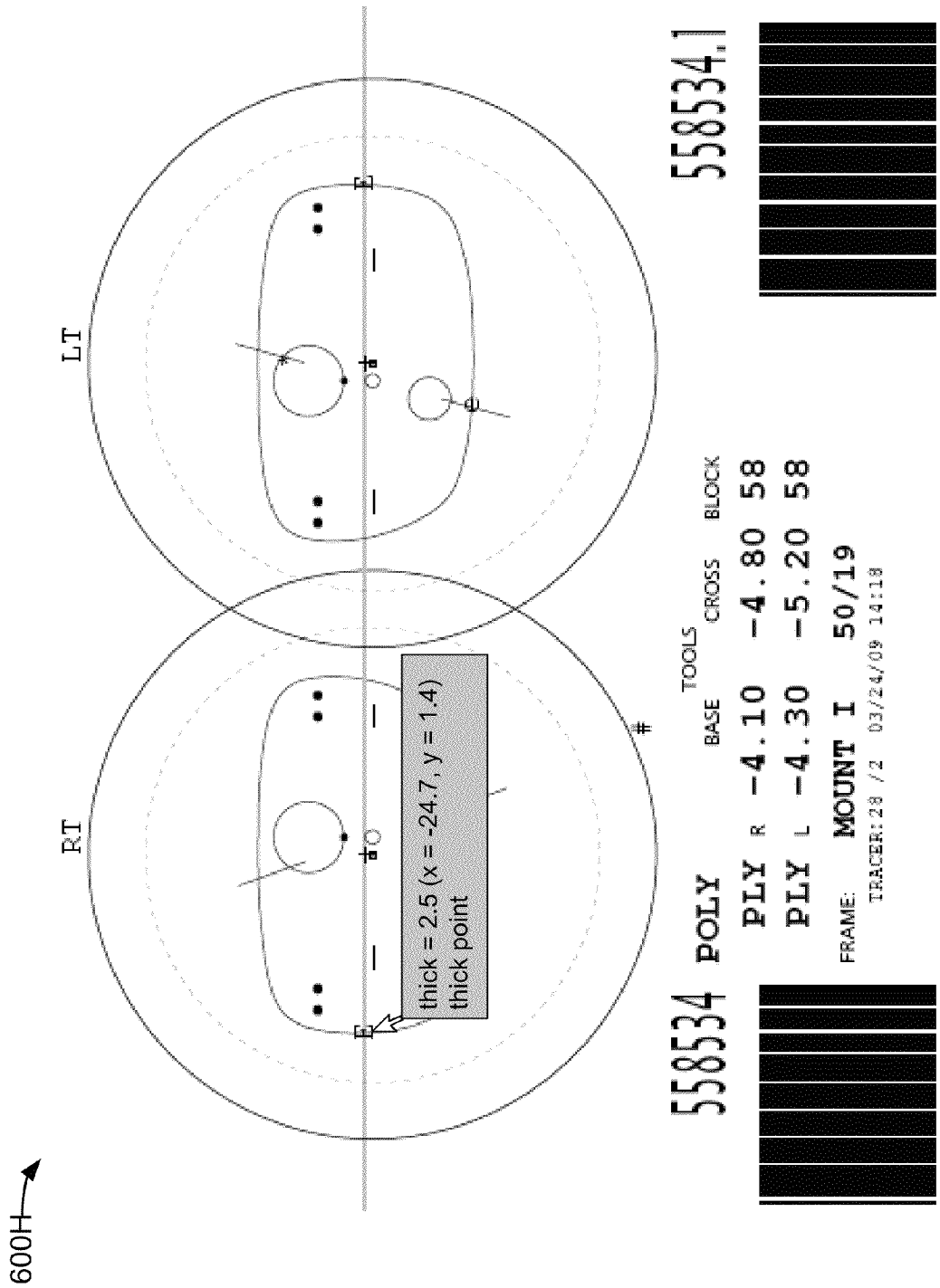

FIGS. 6A-6H are examples of graphical work tickets showing supplemental information about a lens for use in a rimless pair of eyeglasses. When a user moves a cursor over the graphical work ticket, information about the lens, such as the thickness, the coordinates of the cursor location on the lens, and any special information relating to a particular point is provided. FIG. 6A provides the information relating to a first drill point; FIG. 6B shows the information relating to a second drill point; FIG. 6C shows the information relating to the optical center of the lens; FIG. 6D provides the information relating to the lens block center; FIG. 6E provides the information relating to the frame center; FIG. 6F shows the information relating to the near sighting circle, where the near sighting circle is the region of the lens used by the patient for looking at objects close to the user; FIG. 6G provides the information relating to the thinnest point of the lens; and FIG. 6H shows the information relating to the thickest point of lens.

As can be seen from FIGS. 6A-6H, tool tips is an effective way to depict the geometry of the lens processing job. Traditionally, three-dimensional portrayals of the lenses have been used where the lens is shown on a three-dimensional grid that can be rotated. However, with the graphical work ticket, the laboratory technician can use the tool tips only if necessary, thus avoiding cluttering the work ticket with excessive information. Moreover, the laboratory technician will always be oriented to look at the lenses as they would be seen on a patient's face. Thus, the layout is more intuitive, and the likelihood of the laboratory technician making a mistake in translating the information from the graphical work ticket to the lens being processed is reduced.

Figure 7:
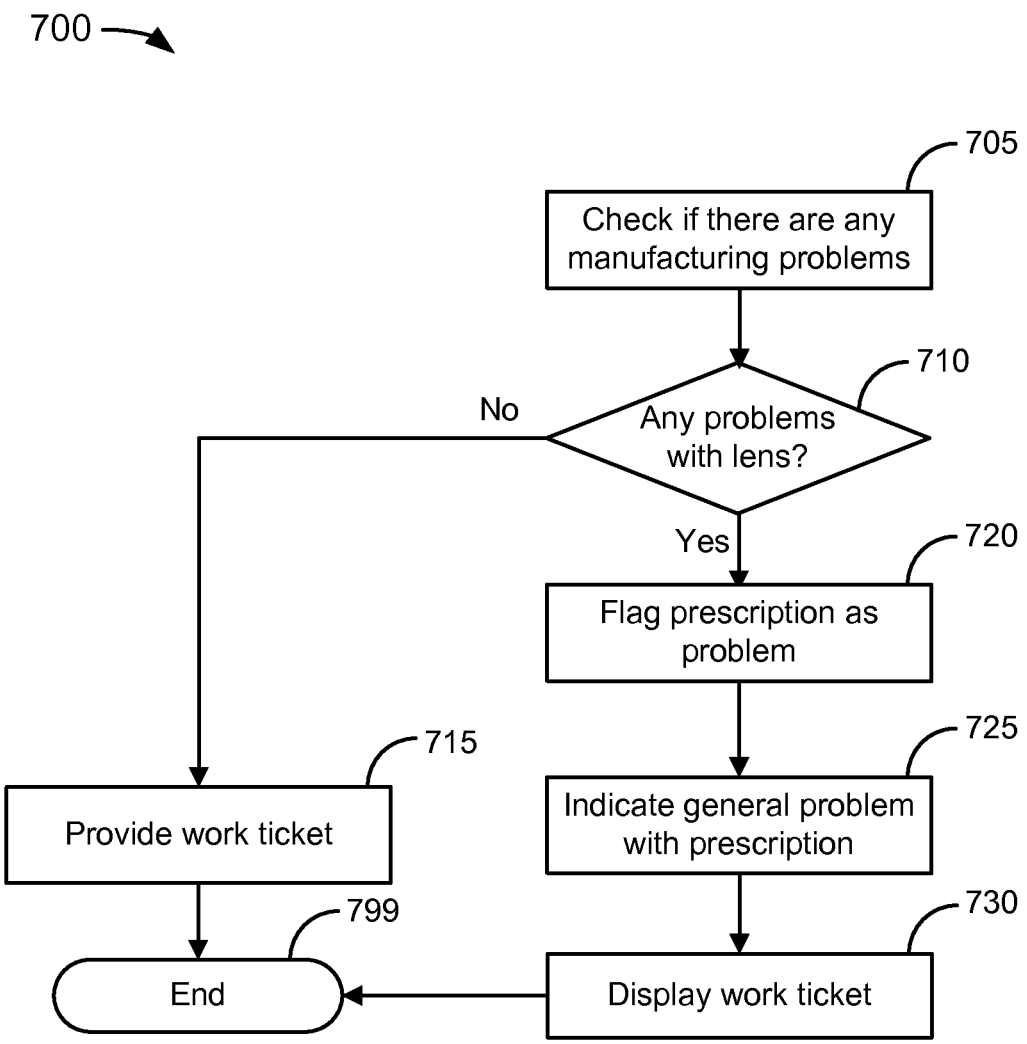
FIG. 7 is a flow chart illustrating an example of a method of displaying a problem with an eyeglass prescription order.

Because many different complicated combinations of eyeglass parameters can be specified by the ECP and/or patient, there is a good possibility that the resulting lens request may turn out to be impossible to manufacture. FIG. 7 is a flow chart illustrating an example of a method 700 of displaying a problem with an eyeglass prescription order. At block 705, the system checks the prescription calculation against the prescription order. Then at decision block 710, the system determines if there are any problems or inconsistencies that would prevent the lens prescription request from being processed. If there are no problems (block 710—No), at block 715 the system provides the work ticket for the prescription request, and the process ends at block 799.

If there are problems with the prescription request (block 710—Yes), at block 720, the system flags the prescription as a manufacturing problem. Then at block 725, the system indicates the particular difficulties with manufacturing the prescription. The system displays the work ticket with appropriate tool tip information that address the prescription manufacturing difficulties at block 730. At this point, the technician can examine the work ticket and bring up the relevant tool tips to determine the source of the problem and discuss the problem along with potential solutions with the requesting ECP. For example, the tool tips can show a warning to check the frame thickness. Then the technician can bring up a screen that shows the drill points in the lens and determine that the lens blank is not appropriate for a particular drill mounting requested for the rimless frame requested in the eyeglass order. The process ends at block 799.

In one example, the tool tip information provided by the system at block 730 can include a list of recommended options for manufacturing the lens or lenses. For example, the system can recommend changing to a higher refractive index lens material or using an aspheric curve on the lens. However, because these recommendations impact the final lens prescription, the lab technician cannot automatically act upon these recommendations. The system provides the recommendations to the technician as a starting point for discussions with the prescribing ECP in an attempt to develop a design that satisfies the ECP's requirements and the patient's preferences.

Suitable Systems

Figure 8:
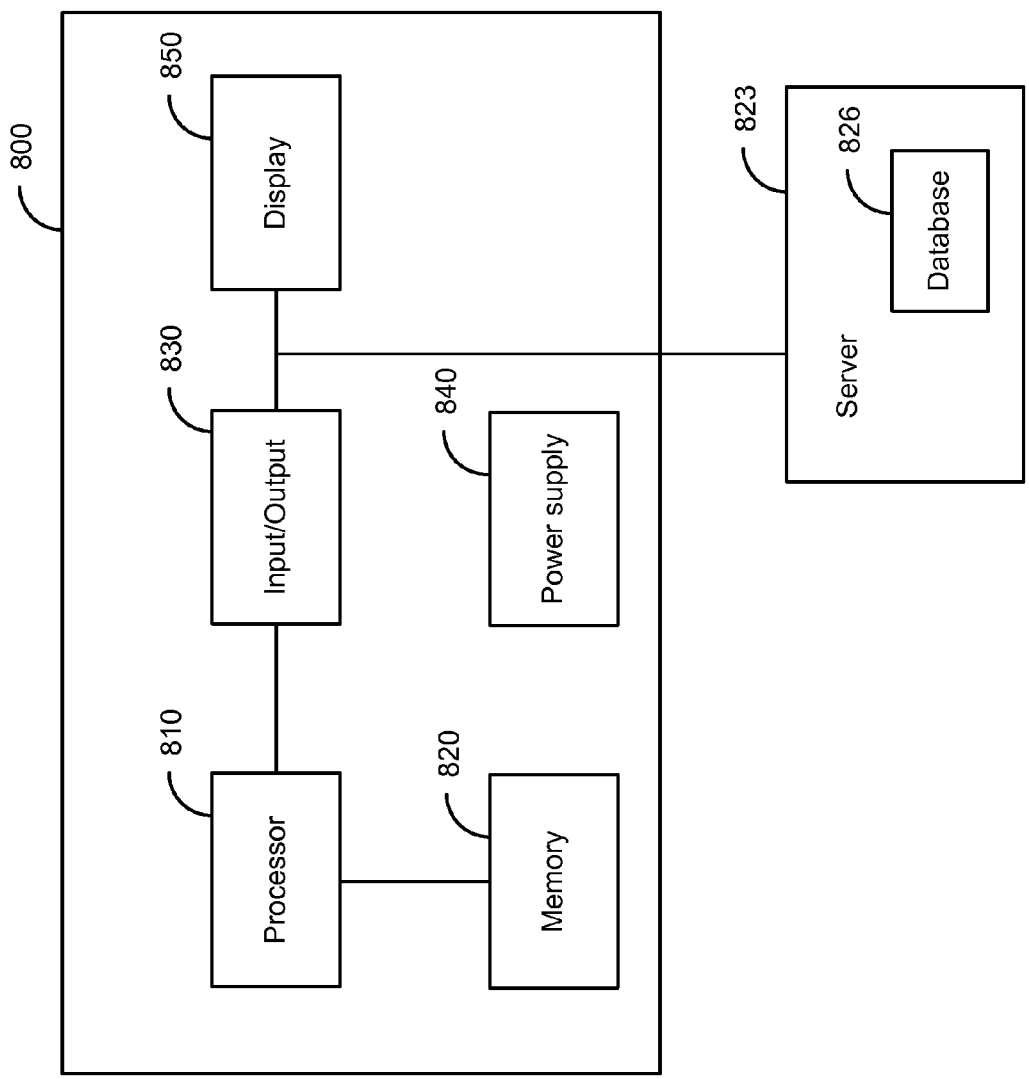
FIG. 8 depicts a block diagram illustrating an example of a user interface system that displays supplemental information for a lens manufacturing work ticket.

FIG. 8 depicts a block diagram illustrating an example of a user interface system 800 that displays supplemental information for a lens manufacturing work ticket through the use of tool tips. The user interface system 800 can include one or more processors 810, memory units 820, input/output devices 830, power supplies 840, and displays 850. The user interface system 800 can access a server 823 that has one or more databases 826. Alternatively, the user interface system 800 can include the server 823 and databases 826.

A processor 810 can be used to control the user interface system 800. Memory units 820 include, but are not limited to, RAM, ROM, and any combination of volatile and non-volatile memory. Input/output devices 830 can include, but are not limited to, triggers to start and stop the user interface system 800, visual displays, speakers, and communication devices that operate through wired or wireless communications, such as a mouse for controlling a cursor. In one embodiment, the input/output device 830 can communicate with a server 823 that has one or more databases 826. The server 823 provides access to files stored in the database 826 and/or other additional information. In one embodiment, the database 826 can include supplemental information to be displayed using tool tips for each of the work elements, and the database can also provide directions for how to recalculate the values and parameters that need to be displayed as part of the supplemental information.

A power supply 840 can include, but is not limited to, a battery. A display 850 can include, but is not limited to, an electronic display.

CONCLUSION

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. For example, while lenses for eyeglasses are mentioned, any type of lens may be processed under the principles disclosed herein. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or subcombinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. (Any claims intended to be treated under 35 U.S.C. §112, ¶6 will begin with the words "means for.") Accordingly, the applicant reserves the right to add additional claims after filing the application to pursue such additional claim forms for other aspects of the invention.

We claim:

1. An electronic lens processing system to facilitate the manufacture of lenses in a laboratory, comprising:
    a display;
    at least one memory component storing a software program and supplemental information,
        wherein the supplemental information includes laboratory information, and
        wherein the laboratory information pertains to equipment, tools, or materials at the laboratory used to physically machine a lens from a lens blank in the laboratory;
    at least one input/output device;
    a processor coupled among the display, the memory component, and the input/output device,
        wherein the processor is configured to execute the software program, the software program comprising:
        a first module operable to perform calculations based at least upon a received lens order and the laboratory information to generate a work ticket for the lens and to store information about the calculations and the laboratory information in the memory component as the supplemental information,
            wherein the lens order specifies a prescription and parameters for the lens, and the work ticket includes at least some of the laboratory information for physically machining the lens specified by the lens order from the lens blank at the laboratory;
        a second module operable to show on the display at least a portion of the work ticket and receive information regarding a position of a cursor or pointer movable by a user and shown in the display; and
        a third module operable to provide a portion of the supplemental information on the display corresponding to an element of the displayed work ticket indicated by the position of the cursor or pointer.

2. The system of claim 1, wherein the laboratory information includes lens stock data.

3. The system of claim 2, wherein the lens stock data includes at least one of: style attributes, material attributes, recommended lens base curve selection information for use with particular lens prescriptions, lens technical information, lens blank inventory in the laboratory, lens pick lists for which manufacturer's lens blank and which lens size to use for the prescription.

4. The system of claim 1, wherein the laboratory information includes frame stock data.

5. The system of claim 4, wherein the frame stock data includes at least one of: frame size availability; frame color availability; whether a given frame is available for requested eye, bridge, or temple measurements; minimum lens edge thickness for a given frame and a compatible lens base curve for a given frame.

6. The system of claim 1, wherein the laboratory information includes surfacing data.

7. The system of claim 6, wherein the surfacing data includes at least one of: setup files for a generator machine, an amount of prism the generator machine can produce in a generated lens, information about dimensions of blocks used to hold lenses in the generator machine, information about tools the generator machine uses to grind lenses and pads placed on the tools, and gauge data about the type of gauge used to measure lens curves and thicknesses.

8. The system of claim 1, wherein the laboratory information includes finishing data.

9. The system of claim 8, wherein the finishing data includes at least one of: whether a coating is compatible with a particular tint, whether a coating is compatible with a particular lens material, adjustments made to the prescription to account for how a given frame fits a patient's face, a position of drill holes, and a shape of drill holes.

10. The system of claim 1, wherein the laboratory information further includes information specific to an account or a lens prescribing doctor.

11. The system of claim 1, wherein the laboratory information includes information about lap tools used by the laboratory and specific lap tools and blocks for manufacturing the lens.

12. The system of claim 1, wherein the laboratory information includes instructions for setting up lens fabrication equipment used to physically machine the lens from the lens blank.

13. The method of system 1, wherein the work order is in a graphical format showing the lens to be processed with lens blank manufacturer markings, and further wherein the laboratory information includes definitions for the markings.

14. The system of claim 1, wherein the laboratory information further includes prescription manufacturing difficulties or recommended options for manufacturing the lens.

15. A computer-implemented method of providing supplemental information in an electronic lens processing system for a facility, comprising:
    receiving by the electronic lens processing system a lens order,
        wherein the lens order specifies a prescription and parameters for a lens;
    performing calculations by the electronic lens processing system based at least upon the received lens order and facility information to generate a work order for the lens, wherein the facility information pertains to equipment, tools, or materials at the facility used to physically machine a lens from a lens blank at the facility;

storing information about the calculations and the facility information as the supplemental information, and wherein the work order includes the facility information for physically machining the lens specified by the lens order from the lens blank at the facility;

displaying by the electronic lens processing system at least a portion of the work order on a screen;

detecting by the electronic lens processing system a selection by a user of an item on the work order displayed on the screen;

in response to detecting by the electronic lens processing system the selection by the user, displaying by the electronic lens processing system previously undisplayed supplemental information corresponding to the selected item on the screen.

16. The method of claim 15, wherein the facility information includes lens stock data and frame stock data.

17. The method of claim 15, wherein the facility information includes surfacing data and finishing data.

18. A computer-readable medium encoded with processing instructions for implementing a method performed by a computer, the method comprising:

receiving a lens order,
wherein the lens order specifies a prescription and parameters for a lens;

performing calculations based at least upon the received lens order and laboratory data to generate a work ticket for the lens, wherein the laboratory data pertain to equipment, tools, or materials at a laboratory used for fabricating lenses at the laboratory;

storing information about the calculations and the laboratory data as supplemental information, wherein the supplemental information includes information for physically fabricating the lens from a lens blank;

providing a work ticket based on the lens order, wherein the work ticket includes the laboratory data for physically fabricating the lens described by the lens order from the lens blank at the laboratory;

displaying at least a portion of the work ticket on a screen;

detecting a selection by a user of an item on the work ticket displayed on the screen; and in response to detecting the selection by the user, displaying previously undisplayed information corresponding to the item on the screen.

19. The computer-readable medium of claim 18, wherein the laboratory data includes lens stock data and frame stock data.

20. The computer-readable medium of claim 18, wherein the laboratory data includes information about lap tools used by the laboratory and specific lap tools and blocks for manufacturing the lens.

* * * * *

UNITED STATES PATENT AND TRADEMARK OFFICE
CERTIFICATE OF CORRECTION

| | |
|---|---|
| PATENT NO. | : 8,639,372 B2 |
| APPLICATION NO. | : 13/718025 |
| DATED | : January 28, 2014 |
| INVENTOR(S) | : Douglas S. Hagen |

Page 1 of 1

It is certified that error appears in the above-identified patent and that said Letters Patent is hereby corrected as shown below:

In the Specification:

In column 4, line 42, delete "system" and insert -- system. --, therefor.

In the Claims:

In column 12, line 51, in claim 13, delete "method of system" and insert -- system of claim --, therefor.

Signed and Sealed this
Third Day of June, 2014

Michelle K. Lee
*Deputy Director of the United States Patent and Trademark Office*